United States Patent
Geissler et al.

(10) Patent No.: US 10,768,167 B2
(45) Date of Patent: Sep. 8, 2020

(54) PLASMA MEMBRANE CITRATE TRANSPORTER FOR USE IN THE DIAGNOSIS AND TREATMENT OF CANCER

(71) Applicant: Universitätsklinikum Regensburg, Regensburg (DE)

(72) Inventors: Edward Geissler, Regensburg (DE); Maria Mycielska, Regensburg (DE); Petra Rümmele, Regensburg (DE)

(73) Assignee: Universitätsklinikum Regensburg, Regensburg (DE)

( * ) Notice: Subject to any disclaimer, the term of this patent is extended or adjusted under 35 U.S.C. 154(b) by 366 days.

(21) Appl. No.: 15/514,255

(22) PCT Filed: Sep. 25, 2015

(86) PCT No.: PCT/EP2015/072098
§ 371 (c)(1),
(2) Date: Mar. 24, 2017

(87) PCT Pub. No.: WO2016/046367
PCT Pub. Date: Mar. 31, 2016

(65) Prior Publication Data
US 2017/0241981 A1    Aug. 24, 2017

(30) Foreign Application Priority Data
Sep. 25, 2014 (EP) ..................... 14186315

(51) Int. Cl.
| G01N 33/50 | (2006.01) |
| C12Q 1/6886 | (2018.01) |
| G01N 33/574 | (2006.01) |
| C07K 16/18 | (2006.01) |
| A61K 39/00 | (2006.01) |

(52) U.S. Cl.
CPC .......... *G01N 33/5011* (2013.01); *C07K 16/18* (2013.01); *C12Q 1/6886* (2013.01); *G01N 33/57492* (2013.01); *A61K 2039/505* (2013.01); *C07K 2317/76* (2013.01); *C12Q 2600/158* (2013.01); *G01N 2500/04* (2013.01); *G01N 2500/10* (2013.01); *G01N 2800/56* (2013.01)

(58) Field of Classification Search
None
See application file for complete search history.

(56) References Cited

FOREIGN PATENT DOCUMENTS

| WO | WO 2004/100885 A2 | 11/2004 |
| WO | WO 2014/066320 A1 | 5/2014 |

OTHER PUBLICATIONS

Mazurek et al. Molecular origin of plasma membrane citrate transporter in human prostate epithelial cells. (EMBO Rep. 11(6): 431-437. Published online May 7, 2010).*
Mycielska, Maria E. et al. Extracellular Citrate Affects Critical Elements of Cancer Cell Metabolism and Supports Cancer Development (Cancer Research 78(10): 2513-2523, published online Mar. 6, 2018).*
Brar et al. (Molecular Cancer Therapeutics 3(9): 1049-1060, 2004).*
Eby (Medical Hypotheses 64: 1124-1126, 2005).*
Cao et al., "NMR-based metabolomic analysis of human bladder cancer," Anal. Sci., vol. 28, No. 5, pp. 451-456 (May 2012).
Cardaci et al., "TCA Cycle Defects and Cancer: When Metabolism Tunes Redox State," Int. J. Cell Biol., vol. 2012 Artlcle ID 161837. pp. 1-9 (2012).
Currie, et al., "Cellular Fatty Acid metabolism and cancer," Cell. Metab., vol. 18, No. 2, pp. 153-161 (Aug. 6, 2013).
Dettmer, et al., "Distinct metabolic differences between various human cancer and primary cells," Electrophoresis, vol. 34, pp. 2836-2847 (2013).
European Search Report corresponding to European Patent Application No. EP14186315 dated Mar. 31, 2015.
Evans, A.J., "Alpha-methylacyl CoA racemase (P504S): overview and potential uses in diagnostic pathology as applied to prostate needle biopsies," J. Clin. Pathol., vol. 56, No. 12, pp. 892-897 (Dec. 2003).
Holla, et al, "Nuclear orphan receptor NR4A2 modulates fatty acid oxidation pathways in colorectal cancer," J. Biol. Chem., vol. 286, No. 34, pp. 30003-30009 (Aug. 26, 2011).
International Search Report corresponding to European patent application No. PCT/EP2015/072098 dated Nov. 11, 2015.
Jang, et al., "Serine/Arginine Protein-Specific Kinase 2 Promotes Leukemia Cell Proliferation by Phosphorylating Acinus and Regulating Cyclin A1," Cancer Res., vol. 68, No. 12, pp. 4559-4570 (23 pages) (Jun. 15, 2008).
Kolukula et al., "SLC25A 1, or CIC, is a novel transcriptional target of mutant p53 and a negative tumor prognostic marker", Oncotarget, vol. 5, No. 5, pp. 1212-1225 (Mar. 2014).
Lang et al., "Mammalian target of rapamycin is activated in human gastric cancer and serves as a target for therapy in an experimental model," Int. J. Cancer, vol. 120, No. 8, pp. 1803-1810 (Apr. 15, 2007).
Linher-Melville et al, "Establishing a relationship between prolactin and altered fatty acid β-oxidation via carnitine palmitoyl transferase 1 in breast cancer cells," BMC Cancer, pp. 11-15 (2011).
Liu, Y., "Fatty acid oxidation is a dominant bioenergetic pathway in prostate cancer." Prostate Cancer Prostatic Dis., vol. 9, No. 3, pp. 230-234 (May 9, 2006).
Mazure et al., "Molecular origin of plasma membrane citrate transporter in human prostate epithelial cells", EMBO reports, vol. 11, No. 6, pp. 431-437 (May 7, 2010).

(Continued)

*Primary Examiner* — Alana Harris Dent
(74) *Attorney, Agent, or Firm* — Jenkins, Wilson, Taylor & Hunt, P.A.

(57) ABSTRACT

The present invention is directed to a method for the diagnosis of cancer involving the plasma membrane citrate transporter (pmCiC). The invention is further directed to a modified substrate or modulator of pmCiC, the use of pmCiC as a tumor marker and a method of screening for a modulator of pmCiC activity.

2 Claims, 17 Drawing Sheets

Specification includes a Sequence Listing.

(56) References Cited

OTHER PUBLICATIONS

Metallo et al., "Reductive glutamine metabolism by IDH1 mediates lipogenesis under hypoxia," Nature, vol. 481, No. 7381, pp. 380-384 (Nov. 2011).

Migita, et al., "ATP Citrate Lyase: Activation and Therapeutic Implications in Non-Small Cell Lung Cancer," Cancer Res., vol. 68, No. 20, pp. 8547-8554 (Oct. 2008).

Mizuno et al., "Impact of Drug Transporter Studies on Drug Discovery and Development," Pharmacological Reviews, vol. 55, No. 3, pp. 425-461 (2003).

Mycielska et al., "Expression of Na+-dependent citrate transport in a strongly metastatic human prostate cancer PC-3M cell line: regulation by voltage-gated Na+ channel activity," J. Physiol., vol. 563, No. 2, pp. 393-408 (2004).

Mycielska et al., "Citrate transport and metabolism in mammalian cells", BioEssays, vol. 31, pp. 10-20 (Jan. 2009).

Ratcliffe, Fumarate hydratase deficiency and cancer: activation of hypoxia signaling?, Cancer Cell, vol. 11, pp. 303-305 (Apr. 2007).

Singh et al., "Mitochondrial aconitase and citrate metabolism in malignant and nonmalignant human prostate tissues," Mol. Cancer, vol. 5, pp. 1-8 (Apr. 2006).

Son et al., "Glutamine supports pancreatic cancer growth through a KRAS-regulated metabolic pathway," Nature, vol. 496, No. 7443, pp. 101-105 (16 pages) (Apr. 2013).

Sun et al., "Mitochondrial and Plasma Membrane Citrate Transporters: Discovery of Selective Inhibitors and Application to Structure/Function Analysis," Mol Cell Pharmacol, vol. 2, No. 3, pp. 101-110 (15 pages) (2010).

Teicher et al., "Antibody Conjugate Therapeutics: Challenges and Potential," Clin Cancer Res., vol. 17, No. 20, pp. 6389-6397 (Oct. 2011).

Van der Goot, et al., "Delaying aging and the aging-associated decline in protein homeostasis by inhibition of tryptophan degradation," PNAS, vol. 109, No. 37, pp. 14912-14917 (2012).

Vander Heiden et al., "Understanding the Warburg effect: the metabolic requirements of cell proliferation," Science, vol. 324, No. 5930, pp. 1029-1033 (12 pages) (May 2009).

Clyne (Mar. 2012) Biopsy citrate concentration could predict prostate cancer growth rate. Nat. Rev. Urol. 9:123.

Costello et al. (1997) Citrate metabolism of normal and malignant prostate epithelial cells. Urology 50(1):3-12.

Cuperlovic-Culf et al. (2012) Targeting the latest hallmark of cancer: another attempt at 'magic bullet' drugs targeting cancers' metabolic phenotype. Future Oncol. 8:1315-1330.

Dittrich et al. (2012) Prostate cancer growth and citrate levels. Prostate Cancer and Prostatic Diseases 15: 278-282.

Dolce et al (2014) Mitochondrial tricarboxylate and dicarboxylate-Tricarboxylate carriers: from animals to plants. IUBMB LIFE 66(7):462-471.

Frezza et al. (2009) Mitochondria in cancer: not just innocent bystanders. Semin. Cancer Biol. vol. 19:4-11.

Icard et al. (2012) Understanding the central role of citrate in the metabolism of cancer cells. Biochimica et Biophysica Acta (BBA) 1825:111-116.

Kohler & Milstein (Aug. 7, 1975) Continuous cultures of fused cells secreting antibody of predefined specificity. Nature (256):495-497.

Kozbor & Roder (1983) The production of monoclonal antibodies from human lymphocytes. Immunology Today 4(3):72-79.

Lantow et al. (2006) Comparative study of cell cycle kinetics and induction of apoptosis or necrosis after exposure of human Mono Mac 6 cells to radiofrequency radiation. Radiat. Res. 166:539-543.

Rocha et al. (2011) Metabolic signatures of lung cancer in biofluids: NMR-based metabonomics of blood plasma. J. Proteome Res. 10:4314-4324.

Serkova et al. (2008) The metabolites citrate, myo-inositol, and spermine are potential age-independent markers of prostate cancer in human expressed prostatic secretions. Prostate 68:620-628.

Zhang et al. (2012) Distinguishing pancreatic cancer from chronic pancreatitis and healthy individuals by (1)H nuclear magnetic resonance-based metabonomic profiles. Clin. Biochem. 45:1064-1069.

IPRP and Written Opinion corresponding to International application No. PCT/EP2015/072098 dated Mar. 28, 2017.

\* cited by examiner

Figure 2 A
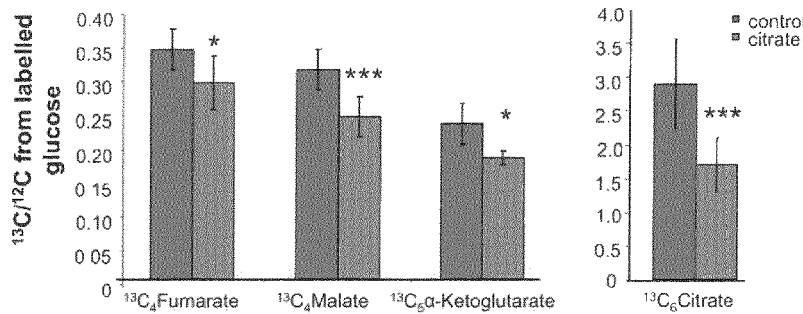
B
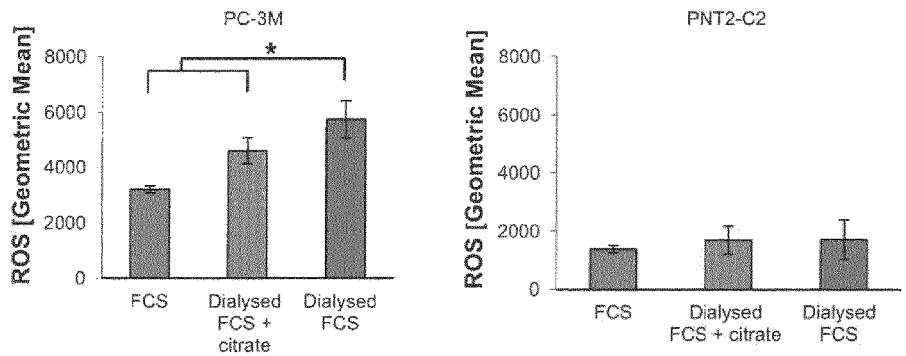
C
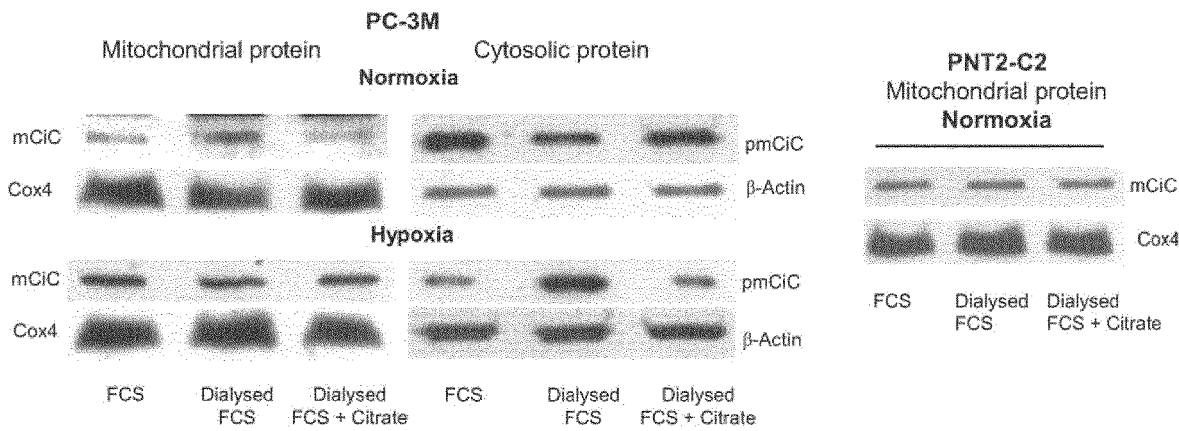
D
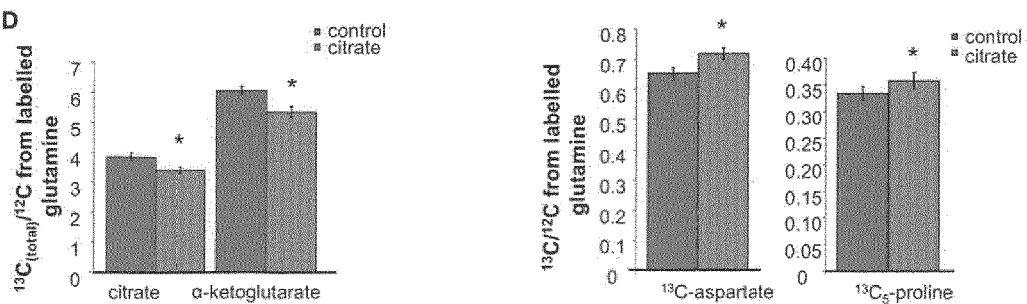

PLASMA MEMBRANE CITRATE TRANSPORTER FOR USE IN THE DIAGNOSIS AND TREATMENT OF CANCER

FIELD OF THE INVENTION

The present invention is directed to a method for the diagnosis of cancer involving the plasma membrane citrate transporter (pmCiC). The invention is further directed to a modified substrate or modulator of pmCiC, the use of pmCiC as a tumor marker and a method of screening for a modulator of pmCiC activity.

BACKGROUND OF THE INVENTION

Malignant tumors need an efficient metabolic system to meet demands for energy and substrates necessary for cancer cells to successfully grow and metastasize. Indeed, metabolism of cancer cells has been a subject of intense research for several years. It has been established that cancer cells switch their metabolism from oxidative phosphorylation to glycolysis (called the "Warburg effect") and, unlike most normal cells, they produce large amounts of fatty acids for plasma membrane rebuilding and energy via β-oxidation. A critical question arising from this observation concerns the origin of citrate, which is a primary substrate for fatty acid synthesis.

Normally, citrate is thought to be produced via the Krebs cycle in mitochondria or through glutamine reductive carboxylation. The former possibility is considered less likely in cancer cells, since reduced mitochondrial activity is one of the hallmarks of malignancy. Moreover, cells would need to have a mechanism that would truncate the Krebs cycle to allow for citrate accumulation; evidence for this has not been found. Instead, up to now glutamine has been considered the major source of citrate in cancer cells. While glutamine consumption is increased in cancer, its role in cancer metabolism does not involve exclusively citrate synthesis, but rather the supply of necessary nitrogen for amino acid synthesis. Interestingly, glutamine reductive carboxylation that may lead to citrate synthesis requires increased reverse activity of the Krebs cycle; this possibility remains questionable in light of overall decreased mitochondrial activity in cancer cells.

Additionally, it should be taken into account that the use of this pathway affects cellular metabolic (red/ox) balance, which presents problems for these cells.

Dittrich et al., "Prostate cancer growth and citrate levels", *Prostate Cancer and Prostatic Diseases* (2012) 15, 278-282, studied the potential utility of assessing prostate cancer progression by measuring citrate levels in prostate cancer tissue. They concluded that low levels of citrate in a unit volume correlate with rapidly increasing PSA values, and, therefore, may be used as an indicator of fast-growing prostate cancer. They noted that tissue samples obtained at the time of biopsy may be evaluated for their citrate concentrations for the prediction of prostate cancer growth rates, allowing for the implementation of alternative treatment options and reducing overtreatment.

Mycielska et al., 205: "Expression of $Na^+$-dependent citrate transport in a strongly metastatic human prostate cancer PC-3M cell line: regulation by voltage-gated Na+ channel activity"; *J Physiol.* 2005 Mar. 1; 563: 393-408, describe that normal prostatic epithelial cells have a $K^+$ dependent efflux mechanism for citrate, whereas malignant prostatic epithelial cells have a $Na^+$ dependent transporter system primarily for uptake of citrate.

Mazurek et al., 2010: Molecular origin of plasma membrane citrate transporter in human prostate epithelial cells. *EMBO Rep.* 2010 June; 11(6):431-7. Epub 2010 May 7, present the results of molecular cloning of a citrate transporter from human normal prostate epithelial PNT2-C2 cells. By using rapid amplification of cDNA by PCR, Mazurek et al. determined that the prostatic carrier is an isoform of the mitochondrial transporter SLC25A1 with a different first exon. They confirmed that pmCiC is a major citrate transporter expressed in the plasma membrane of normal human prostate PNT2-C2 cells and non-malignant prostate tissues. However, there is no indication that pmCiC could be used as a tumor marker or as a target for anti-cancer therapy.

Vamsi K. Kolukula et al.: "SLC25A1, or CiC, is a novel transcriptional target of mutant p53 and a negative tumor prognostic marker", Oncotarget, 15 Mar. 2014, p. 1212, describe SLC25A1, or CiC and its potential function to promote tumorigenesis, but do not take into account the potential presence of pmCiC in the cells.

pmCiC and mitochondrial citrate transporter (mCiC) belong to the same gene family. Both proteins are responsible for citrate transport. They have a similar structure, but different physiological functions.

Even though pmCiC and mCiC are coded on the same chromosome they have different start codons and different first exon and intron. Therefore, they cannot be even considered as splice variants because this is not due to alternative splicing. They are two separate genes occupying in-part the same loci.

mCiC is localized in the inner mitochondrial membrane and is responsible for citrate transport from and to mitochondria. pmCiC, on the other hand, is trafficked to the plasma membrane and in the case of cancer cells, imports extracellular citrate into the cytoplasm.

Despite significant amino acid similarities, the two transporters function in a totally different manner. mCiC transports citrate in both directions in an antiport system (citrate out against malate or citrate in, or citrate in against malate or citrate out). pmCiC transports citrate in one direction in a symport system (in cancer cells citrate is transported with $Na^+$ in the same direction).

mCiC is responsible for a proper functioning of mitochondria by facilitating citrate/malate exchange between the mitochondria and cytoplasm. Blocking mCiC will of course result in decreased citrate/malate content in the cytoplasm, but primarily will affect mitochondrial activity by increasing the intra-mitochondrial level of citrate. Localized in the plasma membrane, pmCiC is responsible for citrate uptake from the extracellular space. Blocking or opening of the pmCiC will have no direct bearing on mitochondrial activity (quite the opposite to mCiC, long-term blocking of pmCiC will result in an increase in mitochondrial activity). pmCiC inhibition will only decrease or increase the cytosolic level of citrate.

To summarize, mCiC and pmCiC are two different proteins belonging to the same gene family. They transport citrate but their mode of action, function, localization and physiological meaning for the cell are completely different. Most importantly, mCiC is ubiquitously expressed in the mitochondrial membrane of all cells, whilst pmCiC expression is mainly restricted to cancer cells. Moreover, any specifically designed modulators of pmCiC will not affect mCiC as they will not penetrate the cell membrane.

OBJECT OF THE INVENTION

It is one object of the invention to provide a method for diagnosing cancer which allows a reliable determination of the presence of cancer and the degree of severity as well as aggressiveness of the same. It is a further object of the invention to provide a new therapeutic approach for the targeted attack of tumor cells which, at the same time, does not harm normal cells.

SUMMARY OF THE INVENTION

The inventors found a highly specialized plasma membrane protein to be responsible for citrate uptake in cancer cells, which is called pmCiC. As a plasma membrane protein, pmCiC is useful for both the identification of cancer cells and for targeting tumors therapeutically for destruction.

The present patent application is based on the unexpected finding that cancer cells use substantial amounts of citrate, and importantly, unlike normal cells, derive it largely from the extracellular space via the pmCiC transporter. The following features of the pmCiC make it a novel target for cancer identification and treatment:

1. Normal cells do not need extracellular citrate, with the exception of some specialized cells which express a different transporter. Consistent with the restricted expression of pmCiC in normal tissues, the inventors found pmCiC expression in a wide variety of human cancer cell lines, as well as in human tumor tissue sections. Moreover, expression of the pmCiC increases along with the severity of tumor grade, making it a potential prognostic marker.

2. pmCiC is a plasma membrane protein that transports citrate from the extracellular space into cancer cells. Therefore, cytotoxic molecules could potentially be carried using the transporter molecule or coupled to citrate for specific delivery to cancer cells, thus serving as a drug therapy port.

3. Citrate is an important energy source and is a substrate for the synthesis of critical cellular building blocks (e.g. fatty acids) for cancer cells. Consequently, therapeutic targeting for pmCiC disruption will inhibit cancer development and progression.

The studies on which the invention is based show that a significant portion of citrate needed for cancer cells is taken up from the extracellular space. This was clearly an unexpected finding, because the hypothesis that cancer cells produce citrate intracellularly (mainly through the reductive carboxylation) is a general consensus in the field. Some recently published reports are consistent with our claim; e.g. several metabolomic studies serendipitously indicate that blood citrate levels decrease in cancer patients, which can serve as cancer marker. Decreases in serum citrate have been observed with tumors originating from tissues such as the lung, bladder or pancreas. Moreover, blood clotting that often accompanies metastatic disease is related to decreased citrate levels.

The present studies have focused primarily on human prostatic cells because the prostate gland synthesizes and releases citrate that is necessary to maintain sperm viability and motility. Levels of citrate in the normal prostate are unusually high compared to the average citrate content of blood (up to 180 mM vs 0.2 mM, respectively). Interestingly, extracellular citrate levels are increased in benign prostatic hyperplasia, but levels dramatically drop off when tumors become malignant. This phenomenon has already been used in MR imaging and spectroscopy to diagnose cancer hot spots in the prostate. Therefore, the inventors took on the task to identify carrier(s) responsible for citrate transport through the membrane of prostatic cells.

Regulation of pmCiC expression and function is expected to be critical for cancer cells. Citrate is a weak acid that chelates crucial cell survival ions such as $Ca^{2+}$ or $Mg^{2+}$. Excess citrate in the cytoplasm of even cancer cells would affect e.g. cell cytoskeleton, motility, and also activity of metabolic enzymes which depend on $Ca^{2+}$ or $Mg^{2+}$ availability. More importantly, high levels of intracellular citrate would inhibit fructokinase, one of the major enzymes involved in glycolysis, a pathway that cancer cell metabolism is dependent on. Citrate is, therefore, an important metabolite necessary to support cancer cell metabolism, but can also be dangerous when its import is not strictly regulated. Too little citrate coming into cancer cells would weaken their survival ability by making them less resistant to chemotherapeutics, starvation and less efficient in supplying cell components for proliferation; too much intracellular citrate would lead to cell death through ion chelation as well as cytoskeleton and enzymatic changes (increased intracellular citrate level resulting in cancer cell death has been shown by other groups; Kruspig et al., 2012). Importantly, the need of cancer cells to strictly regulate cytosolic citrate makes them vulnerable to therapeutics designed to either open or close the pmCiC.

This mechanism of extracellular citrate import in prostate cancer cells prompted the inventors to test the possibility that pmCiC is also present in cancers originating from other organs. Indeed, they have now confirmed the presence of pmCiC in the plasma membrane of all cancer cell lines tested (e.g. prostate, gastric, pancreatic and colon).

Furthermore, expression of pmCiC in various human tissues was evaluated by immunohistochemistry (INC). As expected, the plasma membrane citrate transporter is expressed in normal prostate luminal epithelial cells (for export of citrate), but is found at higher levels in prostate cancer cells (for import of citrate). Data from other human cancerous tissues including pancreatic and gastric adenocarcinoma show that the pmCiC expression correlated to tumor grade and/or tumor subtype. Cancer cells also retain citrate transporter expression at metastatic sites such as lymph nodes.

The inventors have shown that contrary to normal cells in which metabolism remains unchanged in the presence of extracellular citrate, extracellular citrate has a significant effect on cancer cell metabolism and activity:

1. Extracellular citrate increases cell division in cancer cells by approximately 20% compared to the control conditions.

2. Cancer cells decrease reactive oxygen species (ROS) synthesis when extracellular citrate is available. This is of particular importance, since decreased synthesis of ROS correlates with a more metastatic behavior of cells, and also increases their resistance to chemotherapy (Maiti, 2012). Therefore, an increase in ROS synthesis by depriving cancer cells of citrate is of therapeutic relevance.

3. The present studies have shown that extracellular citrate intake modifies the utilization of major metabolic pathways in cancer cells by relieving the need for citrate synthesis. This decreased need of citrate synthesis results in an e.g. increased synthesis of amino acids necessary for cell proliferation or decreases the need of glucose uptake, making cells more resistant to starvation conditions.

4. Some activities of cancer cells associated with metastatic behavior including motility, adhesion and endocytosis have been shown to be increased in the presence of extracellular citrate (Mycielska et al., 2006).

In conclusion extracellular citrate affects major metabolic activities of cancer cells allowing them to use their metabolic machinery in a more efficient way and protects them from hostile environmental factors (glucose starvation, chemotherapeutics, etc). Disruptions in citrate transport (via e.g.

therapeutic inhibition) will upset the metabolic balance of cancer cells and weaken their ability to survive.

DETAILED DESCRIPTION OF THE INVENTION

According to a first aspect of the invention, a method for the diagnosis of cancer is provided comprising the steps of:
a) providing a tissue sample or blood sample from a patient,
b) determining the presence and/or amount of plasma membrane citrate transporter (pmCiC) in said sample, wherein the presence and/or amount of said pmCiC is indicative for the existence of cancer and/or cancer aggressiveness in said tissue.

In a first step, the diagnostic method of the present invention requires the provision of a tissue sample or blood sample from a subject. The sample may be obtained from the subject as part of a routine prophylactic medical examination or if the subject is suspected to develop a malignancy. For example, if high prostate specific antigen (PSA) levels between 4 and 10 ng/mL are considered to be suspicious, a prostate biopsy may be performed to obtain a tissue sample for further analysis by determining the presence and/or amount of pmCiC. Then, the presence and the amount of pmCiC may be indicative for the presence, type and stage of prostate cancer.

pmCiC has been described before, for example in Mazurek et al., 2010, supra. The amino acid sequence of pmCiC is as follows:
MFPAALARRPRRPKSGTGEGPERQRPGGSLRSGF-PVPAGGLAGGIEICITFPTEYVKTQLQLDERSHP-PRYRG IGDCVRQTVRSHGVLGLYRGLSSLLYGSIP-KAAVRFGMFEFLSNHMRDAQGRLDSTRGLLCGLGA GVAEAVV VVCPMETIKVKFIHDQTSPNPKYRGFFH-GVREIVREQGLKGTYQGLTATVLKQGSN-QAIRFFVMTSLRNVVYR GDNPNKPMNPLITGVFGA-IAGAASVFGNTPLDVIKTRMQGLEAHKYRNTVVDC GLQILKKEGLKAFYKGTVP RLGRVCLDVAIVFVI-YDEVVKLLNKVWKTD The above amino acid sequence of pmCiC corresponds to SEQ ID NO: 1.

However, the present invention is not restricted to the above pmCiC sequence but extends to variants having the same biological activity, i.e. activity as plasma membrane citrate transporter. As "biological activity" in this context, especially the responsibility for citrate uptake from extracellular space is considered. In particular variants of the protein, for example deletions, insertions and/or substitutions in the sequence, which cause so-called "silent" changes, are considered to be part of the invention.

For example, such changes in the nucleic acid sequence are considered to cause a substitution with an equivalent amino acid. Preferably are such amino acid substitutions the result of substitutions which substitute one amino acid with a similar amino acid with similar structural and/or chemical properties, i.e. conservative amino acid substitutions.

Amino acid substitutions can be performed on the basis of similarity in polarity, charges, solubility, hydrophobic, hydrophilic, and/or amphipathic (amphiphil) nature of the involved residues. Examples for hydrophobic amino acids are alanine, leucine, isoleucine, valine, proline, phenylalanine, tryptophan and methionine. Polar, neutral amino acids include glycine, serine, threonine, cysteine, thyrosine, asparagine and glutamine. Positively (basic) charged amino acids include arginine, lysine and histidine. And, negatively charged amino acids include aspartic acid and glutamic acid.

Further, pmCiC variants according to the present invention are those encoded by nucleic acids which hybridize to the pmCiC coding sequences under high stringency conditions. High stringency hybridization as used herein refers to conditions that permit hybridization of only those nucleic acid sequences that form stable duplex in 0.018M NaCl at 65° C. (i.e., if a duplex is not stable in 0.018M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

In a preferred embodiment, the amount of pmCiC in said tissue or blood sample is measured, wherein the amount is indicative of the degree of severity and aggressiveness of said cancer. As mentioned above, pmCiC is, for example, expressed in normal prostate luminal epithelial cells (for export of citrate), but is found at higher levels in prostate cancer cells (for import of citrate). Data from other human cancerous tissues including prostatic, pancreatic, gastric and breast adenocarcinoma showed that the pmCiC expression correlated to tumor grade. Immunohistochemical staining of pmCiC was positive in the cancerous tissues tested, including pancreatic and gastric adenocarcinomas (FIG. 10). Data obtained by the inventors show a correlation between the intensity of pmCiC staining and tumor subtype for some types of tumors (FIGS. 4, 9, and 10), confirming the correlation of pmCiC expression with cancer aggressiveness. See also FIG. 12 showing the pmCiC mRNA expression in different human tissues.

Generally, the level of expression of pmCiC in tumor tissues is at least 2×, preferably 5×-10× greater than the level of expression in normal tissues (in case that there is an expression of pmCiC in normal tissues which might form the basis for a comparison). If pmCiC is not normally expressed in a given normal (or healthy) tissue, then the presence of pmCiC is by itself indicative for the presence of a malignant tumor. This is, for example, the case in kidney tissue where there is no normal expression of pmCiC. Therefore, the method of the present invention may be used to determine—based on the presence or absence of pmCiC—existence of cancer in kidney tissue.

In case of doubt, i.e. if pmCiC is expressed in both, normal and tumor tissues, a functional test may be performed which allows discrimination between cancerous tissues and normal tissues: if the present pmCiC allows citrate uptake from extracellular space, then this function is indicative for the existence of cancer. The degree of citrate uptake further can be correlated with the aggressiveness of said cancer. This uptake needs to be inhibited by the specific pmCiC inhibitor, as there are other plasma membrane transporters such as e.g. NaCT which transport citrate. It might also be possible to use radiolabeled citrate uptake (or citrate derivative or e. g. an inhibitor or other labelled substance which binds to the transporter) in vivo in the same way fluorodeoxyglucose uptake is detected using a PET scan.

Therefore, pmCiC is a prognostic and/or predictive marker for cancer/cancer progression. Expression level of pmCiC varies among the tumor cells in the same tissue sample. Importantly, increased expression of the transporter has been found focally accentuated at the invasive front of cancer (FIG. 17) and increased expression of pmCiC has been observed also at metastatic sites (as in FIG. 4). Therefore, pmCiC expression correlates with the metastatic activity/metastatic potential of tumor cells. This observation indicates pmCiC expression level as a potential prognostic marker independent of the histopathological tumor grading system. Additionally, expression levels of pmCiC are a predictive marker that indicates sensitivity or resistance to a specific therapy.

In a further preferred embodiment, step b), i.e determining the presence and/or amount of pmCiC in a sample, involves determining the level of expression of pmCiC either on the nucleic acid or protein level. This preferably is done by RT-PCR, DNA/protein microarrays, or antibodies, preferably by immunohistochemistry or ELISA Western Blot. For example, a quantitative evaluation by immunohistochemistry can be performed by providing reference tumor samples of different stages, which have been stained, and by comparing the staining (and thus the level of expression) in a given sample with these reference samples thereby allowing tumor stage determination.

Immunohistochemistry refers to the process of detecting antigens (e.g., proteins such as pmCiC) in cells of a tissue sample by antibody binding. Immunohistochemical staining is widely used in the diagnosis of abnormal cells such as those found in cancerous tumors. Visualising an antibody-antigen interaction can be accomplished in a number of ways, for example by conjugating an antibody to an enzyme such as peroxidase (that may catalyze a colour-producing reaction) or by tagging the antibody to a fluorophore such as fluorescein or rhodamine, amongst others.

ELISA and Western Blot techniques are well known in the pertinent field, as referred to in standard textbooks such as *Biochemistry* 6th Edition (Sixth Ed.), by Jeremy Berg, John Tymoczko & Lubert Stryer. An antibody reaction can also be visualized by standard flow cytometry analysis, if single cells are obtained from tumor samples.

According to a further aspect, the present invention is directed to a modified substrate or modulator of pmCiC for use in the treatment of cancer. This includes the treatment of, for example, prostate, gastric, pancreatic and colon cancer.

As mentioned above, normal cells do not need extracellular citrate, with the exception of some specialized cells which express a different transporter. Consistent with the restricted expression of pmCiC in normal tissues, the inventors found pmCiC expression in a wide variety of human cancer cell lines, as well as in human tumor tissue sections. Therefore, blocking or at least lowering the pmCiC activity is a valuable tool in an attempt to deprive tumor cells of citrate which is an essential substrate. Thereby, tumor cell metabolism, growth and survival can be substantially affected by modulators of pmCiC.

Importantly, also increased, uncontrolled citrate inflow would be detrimental and likely fatal to cancer cells (as discussed above). Therefore, substances able to open (cause increased citrate uptake by cancer cells through pmCiC) are also considered to be potential anticancer drugs. Example of such an opener in the case of citrate transporter (NaCT, a member of the SLC13 family) is $Li^+$ (Inoue at al., 2003). To this extent, a "modulator" as defined herein is any substance capable of lowering or increasing the activity of pmCiC under physiological conditions, i.e. to reduce its capability of transporting citrate into tumor cells or increasing it in an uncontrolled way in the cells. In an ideal case, such a modulator is an inhibitor or opener of pmCiC. These modulators may be selected from the group consisting of an antibody, aptamer, anti-sense RNA, chemicals or siRNA.

An antibody is preferably selected from a group, which consists of polyclonal antibodies, monoclonal antibodies, humanized antibodies, chimeric antibodies and synthetic antibodies. The antibody according to the invention can be additionally linked to a cytotoxic and/or a detectable agent.

For examples, antibody-protein toxin conjugates including plant-derived protein toxins, such as gelonin, ricin, abrin, and pokeweed antiviral protein, and bacterial toxins such as Pseudomonas exotoxin and Diphtheria toxin (and derivatives thereof), might be used. Further, antibody-radionuclide or antibody-drug conjugates could provide the required toxicity. For example, monoclonal antibodies covalently linked to anticancer drugs such as doxorubicin, vinblastine, and methotrexate might be envisioned. An overview of the available technologies may be found in Teicher et al., Antibody Conjugate Therapeutics: Challenges and Potential, Clin Cancer Res 2011; 17:6389-6397.

The term "antibody", is used herein for intact antibodies as well as antibody fragments, which have a certain ability to selectively bind to an epitope. Such fragments include, without limitations, Fab, $F(ab')_2$ and Fv antibody fragments. The term "epitope" means any antigen determinant of an antigen, to which the paratope of an antibody can bind. Epitope determinants usually consist of chemically active surface groups of molecules (e.g. amino acid or sugar residues) and usually display a three-dimensional structure as well as specific physical properties.

The antibodies according to the invention can be produced according to any known procedure. For example the pure complete pmCiC protein or a part of it can be provided and used as an immunogen to immunize an animal and to produce specific antibodies.

The production of polyclonal antibodies is commonly known. Detailed protocols can be found for example in Green et al, Production of Polyclonal Antisera, in Immunochemical Protocols (Manson, editor), pages 1-5 (Humana Press 1992) and Coligan et al, Production of Polyclonal Antisera in Rabbits, Rats, Mice and Hamsters, in Current Protocols In Immunology, section 2.4.1 (1992). In addition, the expert is familiar with several techniques regarding the purification and concentration of polyclonal antibodies, as well as of monoclonal antibodies (Coligan et al, Unit 9, Current Protocols in Immunology, Wiley Interscience, 1994).

The production of monoclonal antibodies is as well commonly known. Examples include the hybridoma method (Kohler and Milstein, 1975, *Nature*, 256:495-497, Coligan et al., section 2.5.1-2.6.7), the trioma technique, the human B-cell hybridoma technique (Kozbor et al., 1983, *Immunology Today* 4:72), and the EBV-hybridoma technique to produce human monoclonal antibodies (Cole, et al., 1985, in Monoclonal Antibodies and Cancer Therapy, Alan R. Liss, Inc., pp. 77-96).

Aptamers as used herein are oligonucleic acid or peptide molecules that bind to a specific target molecule. Aptamers are usually created by selecting them from a large random sequence pool.

Small interfering RNA (siRNA) is a class of double-stranded RNA molecules, 20-25 base pairs in length. It may interfere with the expression of specific genes (such as those encoding pmCiC) with complementary nucleotide sequences. siRNA functions by causing mRNA to be broken down after transcription resulting in no translation. In contrast, antisense RNA is a single-stranded RNA that is complementary to a messenger RNA (mRNA) strand transcribed within a cell. Antisense RNA may be introduced into a cell to inhibit translation of a complementary mRNA by base pairing to it and physically obstructing the translation machinery, therefore not translating proteins such as pmCiC.

A modulator, according to the present invention, might be an enhancer of pmCiC activity as well. Such an enhancer or "opener" could promote pmCiC and thus cancer cell death (see also above).

A "chemical" could be any chemical that would have a modulatory effect on the transport activity. This modifying effect can occur in many different ways e.g. competitive, mechanical etc. The inventors have already tried in the preliminary studies such blockers as 1,2,3 benzenetricarboxylate or mersalyl, also used earlier on the mitochondrial variant of the transporter. Examples of those substances are the following structures:

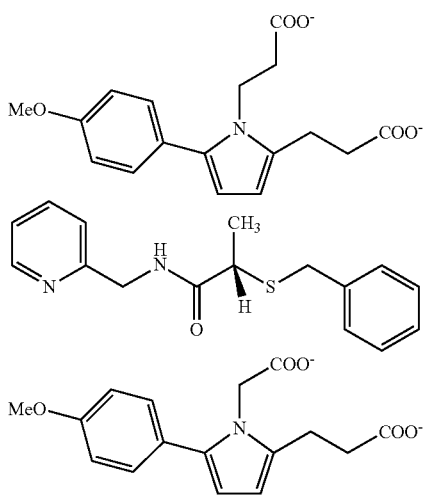

These substances have already been proven as inhibitors of a mitochondrial transporter (mCiC) which has a similar structure as the pmCiC, therefore, they may be effective in potential cancer therapy, see Sun et al., Mitochondrial and Plasma Membrane Citrate Transporters: Discovery of Selective Inhibitors and Application to Structure/Function Analysis, *Mol Cell Pharmacol.* 2010; 2(3): 101-110.

One further preferred and exemplary type of an inhibitor is gluconate. The inventors have shown that gluconate is a potent inhibitor of pmCiC, as it can be seen from the examples and FIGS. 13-16.

Preferably, the amount of gluconate to be administered in vivo is so selected that blood gluconate concentrations of about 400-2,000 µM are obtained.

The term "modified substrate" as used herein preferably means a specific substrate of pmCiC, i.e. a substance which will bind to the binding site of pmCiC. For example, several drugs already used in cancer therapy like e.g. pazopanib, vandetanib, nilotinib, canertinib and erlotinib which are transported by OATPs (organic anion-transporting polypeptide) may be used as such a modified substrate. See the paper of Mizuno et al., Impact of Drug Transporter Studies on Drug Discovery and Development, *Pharmacological Reviews*, 55: 425-461, 2003. Furthermore, a "modified substrate" might be modified citrate or a substance that would mimic citrate as in the case of bestatin (peptide-mimetic anticancer drug transported by PEPT1), but in such a way that it would not have any affinity for the transporters from the SLC13 family. Further, citrate coupled to a cytotoxic agent might be used as a modified substrate as well.

The modulator or modified substrate of the present invention preferably is used in a treatment comprising administering said modulator or modified substrate to a cancer patient in a physiologically suitable dosage form, thereby promoting cancer cell death. The patient may be a human or non-human, for example, animal patient.

The modulator or modified substrate of the present invention is, according to further aspect, provided as a pharmaceutical composition comprising the same and one or more pharmaceutically acceptable auxiliaries or excipients. These are manufactured in a manner which is itself known, for example, by means of conventional dissolving or suspending the compounds, which are all either water soluble or suspendible.

The pharmaceutical preparations which can be used orally include push-fit capsules made of gelatin, as well as soft, sealed capsules make of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste using for example, maize starch, wheat starch, rich starchy, potato starch, gelatin, tragacanth, methylcellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tables or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions that may contain substances which increase the viscosity of the suspension include, for example, sodium carboxymethyl cellulose, sorbitol, and/or dextran. Optionally, the suspension may also contain stabilizers.

In a further general aspect, the invention is directed to the use of pmCiC as a tumor marker. Furthermore, the present invention is directed to the use of a modified substrate or modulator substance for inhibiting pmCiC activity.

In a still further aspect, a method of screening for a modulator of pmCiC activity is provided involving the steps of:
a) providing a test substance,
b) contacting the test substance with pmCiC under suitable conditions, and
c) evaluating whether the test substance effectively modulates the activity of pmCiC.

Preferably, the modulator inhibits or lowers the pmCiC activity, but modulators that increase pmCiC activity could also be used to target tumor cells.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now further illustrated by the accompanying drawings.

DESCRIPTION OF THE DRAWINGS

FIG. 2. Impact of extracellular citrate on Krebs cycle activity. PC-3M cells were incubated for 72 h with 25 mM [U-13C]glucose with or without the addition of 200 µM unlabelled citrate. (A) Differences in the ratio of uniform $^{13}$C incorporation into fully labelled Krebs cycle intermediates. (*P<0.05, ***P<0.005; n=5). (B) Differences in ROS synthesis determined by flow cytometry for PC-3M (left) and PNT2-C2 (right) cells. Cells were incubated in media containing FCS, dialysed FCS+200 µM citrate, or dialysed serum only. Shown are geometric means±SD. (*P<0.05; n=6-9). (C) Differences in pmCiC (in cytoplasm) and mCiC (in mitochondria) expression in PC-3M cells grown for 24 h in media with FCS, dialysed FCS, or dialysed FCS+200 µM citrate under normoxic or hypoxic conditions (left). Changes in mCiC in mitochondrial protein derived from PNT2-C2 cells was also determined under normoxic conditions (right). (D) Labelled glutamine metabolism. PC-3M cells were incubated with 2 mM uniformly $^{13}$C-labelled glutamine, 25 mM of unlabelled glucose±200 µM unlabelled citrate for 24 h. (Left) Differences in the ratio of $^{13}$C incorporation from labelled glutamine into total Krebs cycle intermediates are shown. (*P<0.05; n=5). (Right) Differences in the ratio of $^{13}$C incorporation from labelled glutamine into total $^{13}$C aspartate and $^{13}C_5$ proline are depicted. (*P<0.05; n=5).

FIG. 5. (A-B) Effect of extracellular citrate on intracellular $Ca^{2+}$ levels in PC-3M cells. (A) Average Fura-2 ratio values during the application of 200 µM citrate or 100 µM ATP. (***P<0.005; n=30). (B) Fura-2/AM loaded cells kept in Ringer's solution were subject to the application of 200 µM citrate. The trace shows the average response of 15 cells. ATP and ionomycin were used for controls.

EXAMPLES

Figure 1:
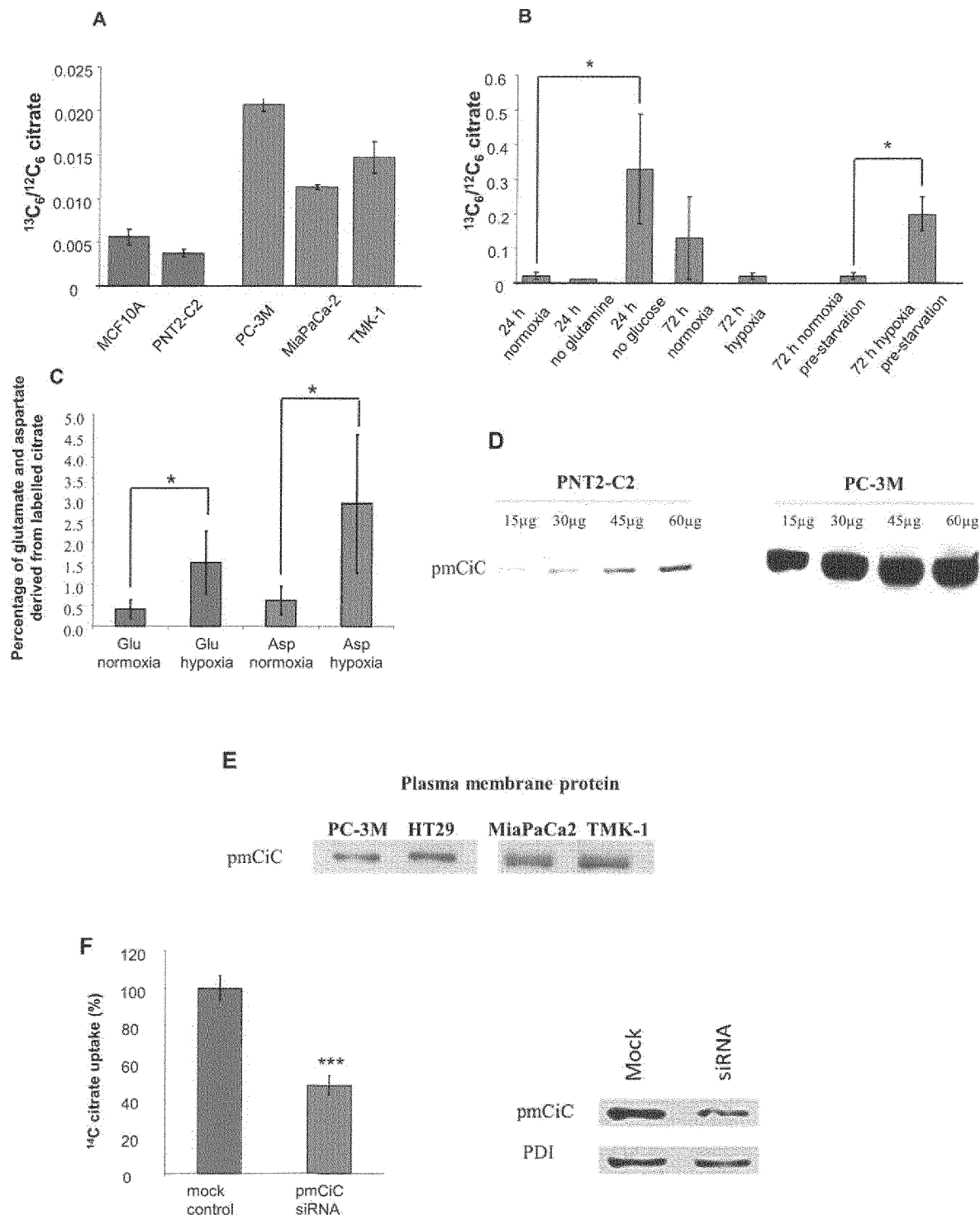
FIG. 1. Basal citrate uptake and molecular origin of the plasma membrane citrate transporter in cancer. (A) Intracellular $^{13}C_6/^{12}C_6$ citrate ratios in normal (MCF10A-breast and PNT2-C2-prostate) and cancer (PC-3M-prostate, TMK-1-gastric and MiaPaCa-2-pancreatic) cell lines incubated with 200 µM [U-$^{13}$C]citrate for 24 h under normoxic conditions in the presence of 10 mM glucose and 2 mM glutamine (n=5). (B) Intracellular $^{13}C_6/^{12}C_6$ citrate in PC-3M grown under different conditions. No glucose (for 24 h) and 72 h hypoxia samples preceded by 24 h glucose starvation showed significantly higher $^{13}$C-citrate uptake into the total intracellular citrate pool. (*P<0.05; n=5). (C) The percentage of fully $^{13}$C-labelled glutamate and aspartate formed from [U-$^{13}$C]citrate compared to $^{13}$C-labelled glutamate and aspartate derived from [U-13C]glucose after 24 h of incubation under normoxic and hypoxic conditions. (*P<0.05; n=5). (D) Expression of pmCiC in total protein derived from PNT2-C2 and PC-3M cells with different protein loadings. (E) Expression of pmCiC in the plasma membrane of prostate, colon, pancreatic and gastric cell lines. (F) Relative to mock transfected PC-3M cells, $^{14}$C citrate uptake is shown for cells with transiently silenced pmCiC (left; ***P<0.005, n=8). pmCiC expression levels in PC-3M mock-transfected cells and cells transiently transfected with siRNA specific for the transporter (right).

To determine if cancer and normal cells take up extracellular citrate present at physiological concentrations, the inventors incubated different cell lines with [U-$^{13}$C]citrate at 200 µM (24 h). Citrate uptake was assessed as the intracellular ratio of fully labelled $^{13}$C to $^{12}$C citrate in prostate (PC-3M), pancreatic (MiaPaCa-2) and gastric (TMK-1) cancer and in non-neoplastic breast (MCF10A) and prostate (PNT2-C2) cell lines. These studies show that cancer cells take up greater amounts of citrate than normal cells (FIG. 1A). Depending on the conditions, up to a third of the total intracellular citrate pool in cancer cells is derived from uptake of extracellular citrate (FIG. 1B); the strongest effects are observed in cells starved of glucose for 24 h and in cells grown for 72 h under hypoxia preceded by 24 h glucose deprivation, confirming active regulation of citrate uptake by cancer cells. We conclude that cancer cells take up extracellular citrate present at physiologically relevant levels, and this uptake is influenced by stress conditions.

We determined the amount of fully labelled intracellular glutamate and aspartate derived from either 25 mM [U-$^{13}$C]-labelled glucose or 200 µM [U-$^{13}$C]-labelled citrate in prostate cancer PC-3M cells using HPLC-MS/MS (FIG. 1C). As low glucose significantly affected citrate metabolism (FIG. 1B), high glucose (25 mM) was used to sustain stable non-starvation conditions; since glutamine has been suggested to be the main source of citrate in cancer cells, it was also present in all experiments (2 mM). By determining the amount of glutamate and aspartate derived from labelled citrate as a percentage of these metabolites originating from labelled glucose, our results demonstrate that extracellular citrate is metabolised (FIG. 1C). Interestingly, under hypoxia, the amount of fully labelled citrate derivatives increased. These results confirm that extracellular citrate is taken up in a controlled way and metabolised by cancer cells.

To exclude the possibility of intracellular $Ca^{2+}$ changes in the presence of extracellular citrate on the observed effects, intracellular $Ca^{2+}$ level was measured using live cell imaging in PC-3M cells loaded with Fura-2 (Supp. FIGS. 1A and B). No significant effect of extracellular citrate on intracellular $Ca^{2+}$ levels was detected, excluding citrate chelation of divalent cations as a possible non-specific action.

Since citrate cannot move freely through cellular membranes, its transport requires a carrier protein. Prostate cancer cells do not express any of the known plasma membrane di/tri-carboxylate transporters belonging to the SLC13 gene family[13]. Interestingly, PCR and Western blotting of PC-3M prostate cancer cells suggest a significant presence of the plasma membrane citrate carrier that was recently cloned from normal prostate PNT2-C2 cells[14] (pmCiC; FIG. 1D). Sequencing of the PCR products confirms that PC-3M cells express pmCiC[14]. Western blot analysis of the plasma membrane proteins from prostate (PC-3M), colon (HT29), pancreatic (MiaPaCa2) and gastric (TMK1) cell lines indicate that expression of the pmCiC is not specific to only prostate cancer (FIG. 1E).

To confirm that pmCiC is responsible for citrate uptake the inventors used siRNA to transiently silence pmCiC in PC-3M cells; indeed, a significantly reduced short-term (13 min) uptake of $^{14}C$-labelled citrate is observed (FIG. 1F). Intracellular content of the $^{13}C$-citrate is also reduced in the presence of two different siRNAs in long term (24 h) experiments (Supp. FIG. 2), confirming the function of pmCiC in extracellular citrate uptake by tumour cells. The pmCiC transporter determined to be expressed in cancer cells and responsible for citrate import has been shown previously to be present in normal prostate epithelial cells, with the function of exporting citrate into the lumen. Interestingly, this transporter has also been found to take up citrate when expressed in HEK cells, suggesting that the directional activity of the pmCiC depends on the cell type and plasma membrane composition[14]. We conclude that cancer cells express pmCiC in their plasma membrane and this protein is responsible for extracellular citrate uptake.

To establish the overall effects of extracellular citrate on cancer cell metabolism, changes in Krebs cycle and glycolysis were determined. We compared incorporation of $^{13}C$ from [U-13C]glucose into intermediates (HPLC-MS/MS) of the Krebs cycle in PC-3M cells in the presence or absence of extracellular citrate. Intracellular metabolite ratios were studied in prostate cancer cells grown under citrate-depleted conditions (dialysed serum) or with 200 μM citrate-supplemented media. Under normoxic conditions the incorporation of labelled carbons from glucose into fully labelled fumarate, malate, α-ketoglutarate and citrate is significantly decreased (13% to 41%) when cells are exposed to extracellular citrate (FIG. 2A).

Figure 7:
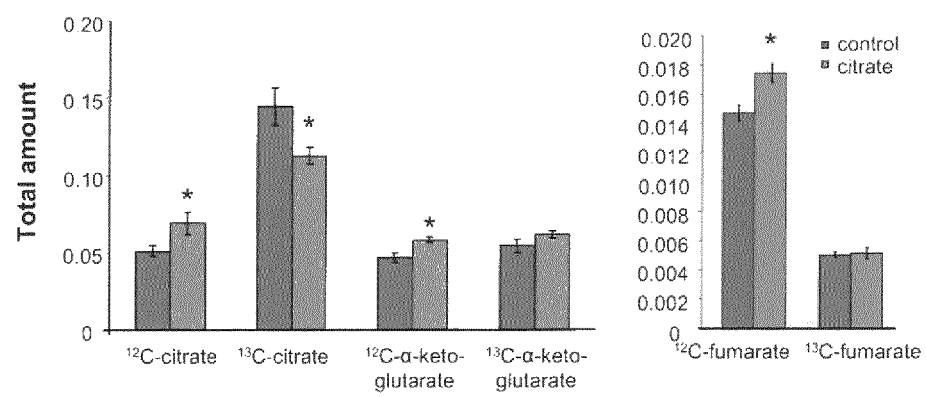
FIG. 7. Influence of extracellular citrate on total amounts of particular Krebs cycle intermediates shown as a normalized response (determined as a ratio of the specific substrate peak area over the total peak areas of measured intermediates; normalization to the total peak area of all analytes corrects for variance in cell growth, sample preparation and analysis). (*P<0.05; n=5).

Changes in Krebs cycle activity were also determined by measuring the absolute amounts determined as a normalized response of the studied substrates (unlabelled and total $^{13}C$ depicting all substrates with any number of labelled carbons) in the presence or absence of unlabelled extracellular citrate (FIG. 7). In the presence of unlabelled citrate, the total amount of intracellular $^{12}C$-citrate, -α-ketoglutarate and -fumarate increased (14-26%). Interestingly, accumulation of fumarate is a reported characteristic of cancer cells[15]. Reciprocally, the inventors observed a 23% decrease in intracellular $^{13}C$-labelled citrate with no change in the amount of labelled α-ketoglutarate and fumarate (FIG. 7). These data confirm that extracellular citrate modifies Krebs cycle activity by increasing intracellular content of substrates derived from non-glucose sources. Using flow cytometry the inventors also determined that ROS levels in PC-3M cells grown with extracellular citrate were decreases by about 20%, compared to cells grown in citrate-depleted dialysed serum (FIG. 2B); use of normal non-dialysed serum also reduces ROS levels. Extracellular citrate did not affect ROS synthesis in normal PNT2-C2 cells (FIG. 2B). Therefore, decreased mitochondrial activity in the presence of extracellular citrate could affect processes such as apoptosis by reducing ROS synthesis.

The increase in unlabelled citrate and α-ketoglutarate, as well as fumarate accumulation, suggest that citrate uptake might partially relieve the requirement for mitochondria to supply citrate for cytoplasmic needs. Therefore, the inventors determined the amount of pmCiC in PC-3M cells in relation to the abundance of mitochondrial citrate transporter (mCiC), under different conditions (FIG. 2C). Under normoxia, in the absence of extracellular citrate there is an increased abundance of mCiC in the mitochondria of PC-3M cells accompanied by a decrease in pmCiC, suggesting that cancer cells can function under different metabolic profiles also depending on the extracellular substrate availability. Interestingly, under hypoxia, the abundance of mCiC is unaffected by the absence of extracellular citrate, whilst there is a substantial increase of pmCiC (FIG. 2C). This differential regulation could be explained by the fact that mitochondrial citrate synthesis cannot be increased in the absence of oxygen, thus inciting an increase in pmCiC. Importantly, expression of mCiC in normal PNT2-C2 cells was insensitive to the presence of extracellular citrate. Furthermore, expression of m- and pmCiC in PC-3M cell is similar under conditions with added citrate and FCS, consistent with the presence of ~200 μM of citrate in serum (measured in media). These results suggest that extracellular citrate is able to influence mitochondrial activity in cancer cells.

Cancer cells take up extracellular glutamine to support their metabolism through reductive carboxylation, however, use of the Krebs cycle intermediates to synthesise glutamine in vivo by human glioblastoma has also been shown recently[16]. We examined the influence of extracellular citrate on glutamine metabolism in PC-3M cells by using [U-13C]glutamine. Cells treated with unlabelled extracellular citrate show a decreased ratio of $^{13}C$ incorporation into citrate and α-ketoglutarate from labelled glutamine (FIG. 2D) accompanied by an increased ratio of the incorporation of $^{13}C$ from glutamine into aspartate and fully labelled proline. This suggests that extracellular citrate supports glutaminolysis, allowing for excess glutamate to be funnelled into proline biosynthesis. Decreased mitochondrial activity permits accumulation of aspartate derived from glutamine; aspartate is a substrate for generation of non-essential amino acids, which are crucial for cancer cell survival[17].

Figure 3:
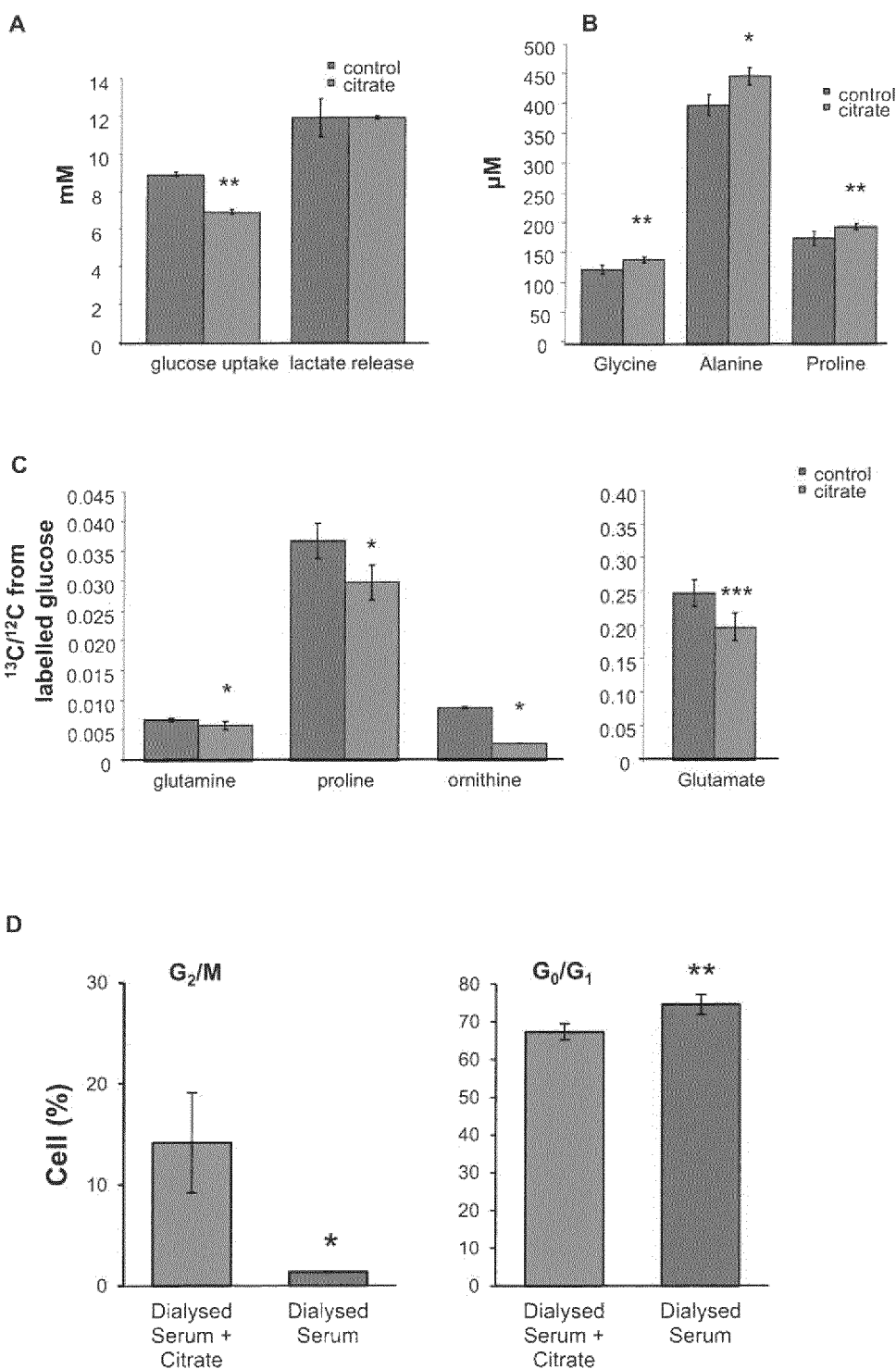
FIG. 3. Glycolytic activity and amino acid release. (A) Amount of glucose consumed and lactate released by PC-3M cells grown for 24 h with or without 200 µM citrate. (**P<0.01; n=5). (B) Concentrations of glycine, alanine and proline in the supernatants of PC-3M cells grown for 72 h with or without 200 µM citrate. (*P<0.05, **P<0.01; n=5). (C) Influence of extracellular citrate on the intracellular ratio of 13C-labeled to unlabelled free amino acids. PC-3M cells were incubated for 72 h in media supplemented with [U-$^{13}$C]glucose with or without 200 µM unlabelled citrate, the ratio of $^{13}$C incorporation into amino acids is shown. (*P<0.05, ***P<0.005; n=5). (D) Cell division in the presence or absence of extracellular citrate under normoxic conditions determined by flow cytometry. (*P<0.05, **P<0.01; n=6).

To assess glycolysis the inventors measured (unlabelled) glucose uptake and lactate release in the media from PC-3M cells incubated±200 μM citrate for 24 h. Interestingly, while lactate production (measured as the absolute amount of lactate per media volume) is unaffected in PC-3M cells incubated with citrate, cells used ~22% less glucose (FIG. 3A). This effect is most likely related to increased conversion of pyruvate to lactate because of decreased mitochondrial citrate synthesis. This result supports our other data suggesting decreased Krebs cycle activity in the presence of extracellular citrate.

Measurements of free amino acids from the media in the presence of extracellular citrate showed increases in the release of glycine, alanine and glutamate-derived proline (11-12%; FIG. 3B). These data support the overall hypothesis that extracellular citrate reduces citrate production needs, allowing for altered metabolism of available substrates. The concentration of other amino acids tested did not differ significantly (data not shown).

Figure 8:
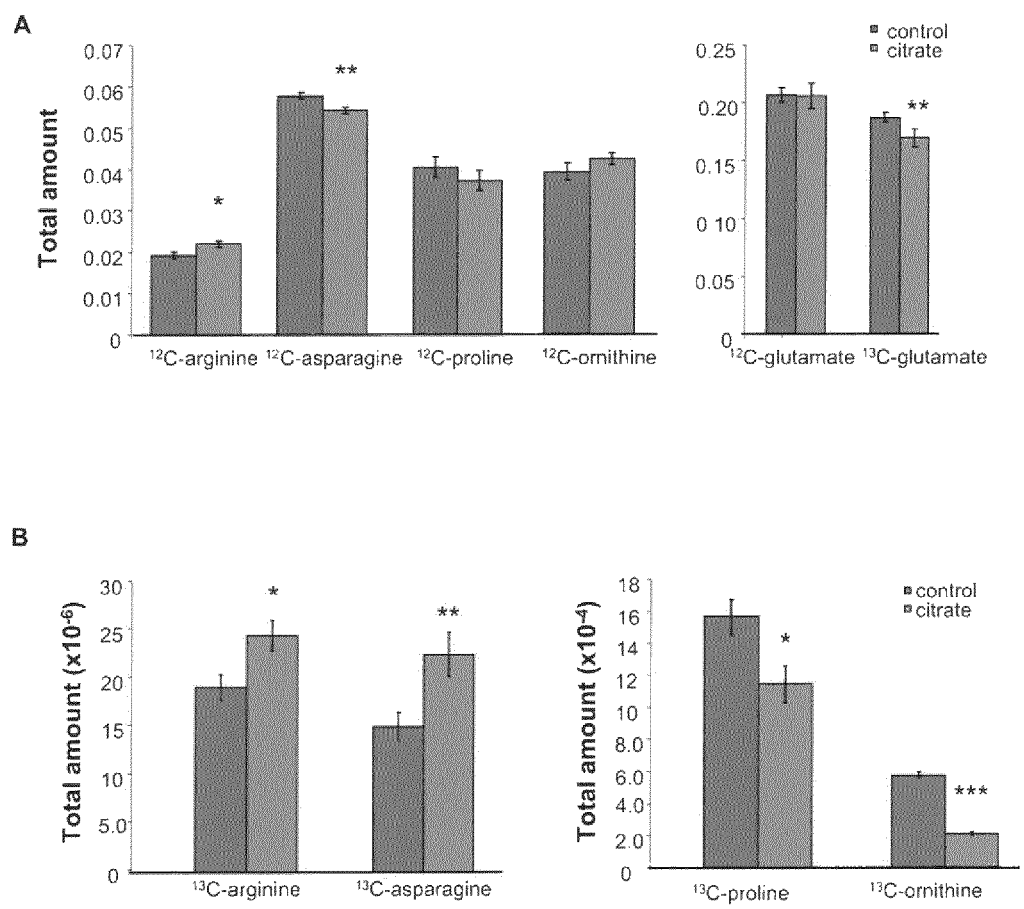
FIG. 8. (A-B) Influence of extracellular citrate on intracellular amino acid levels. PC-3M cells were incubated for 72 h in media supplemented with [U-$^{13}$C]glucose with or without 200 µM unlabelled citrate. Changes in total intracellular amounts of labelled and unlabelled amino acids determined as a normalized response. (*P<0.05, P<0.01, *P<0.005; n=5).

We further examined the effects of extracellular citrate on levels of intracellular free amino acids. PC-3M cells were grown in media supplemented with 25 mM $^{13}C_6$-labelled glucose±200 µM unlabelled citrate. In the presence of extracellular citrate a significant decrease is observed in $^{13}C$ incorporation from labelled glucose into glutamine, proline, ornithine and glutamate (a derivative of α-ketoglutarate) (FIG. 3C). There are also significant increases in absolute amounts of both labelled and unlabelled arginine, as well as labelled asparagine (FIGS. 8A and B), while levels of unlabelled asparagine and labelled proline and ornithine are significantly decreased (FIGS. 8A and B). The levels of unlabelled proline, ornithine and glutamate remained unchanged. $^{13}C$ incorporation ratio into other measured amino acids is unaffected in the presence of extracellular citrate (data not shown). Decreased incorporation of $^{13}C$ derived from labelled glucose is consistent with the synthesis of amino acids from unlabelled sources (e.g. citrate). Amino acids such as arginine are necessary for cancer cell division and survival[18].

An increase in the synthesis of amino acids in the presence of extracellular citrate prompted cell division testing. By microscopic cell counting (trypan blue exclusion) the inventors found that extracellular citrate increased PC-3M cell numbers by 20.3%±2.2% (P=0.003, n=5). These results were corroborated by flow cytometry-based cell division studies that revealed a sharp increase in the $G_2/M$ phase in PC-3M cells cultured with supplemented citrate, whilst there is a decrease in cells entering the non-dividing phase ($G_0/G_1$) (FIG. 3D). Therefore, metabolic changes induced by extracellular citrate affect metabolism to an extent that impacts cellular processes such as cell division.

Figure 4:
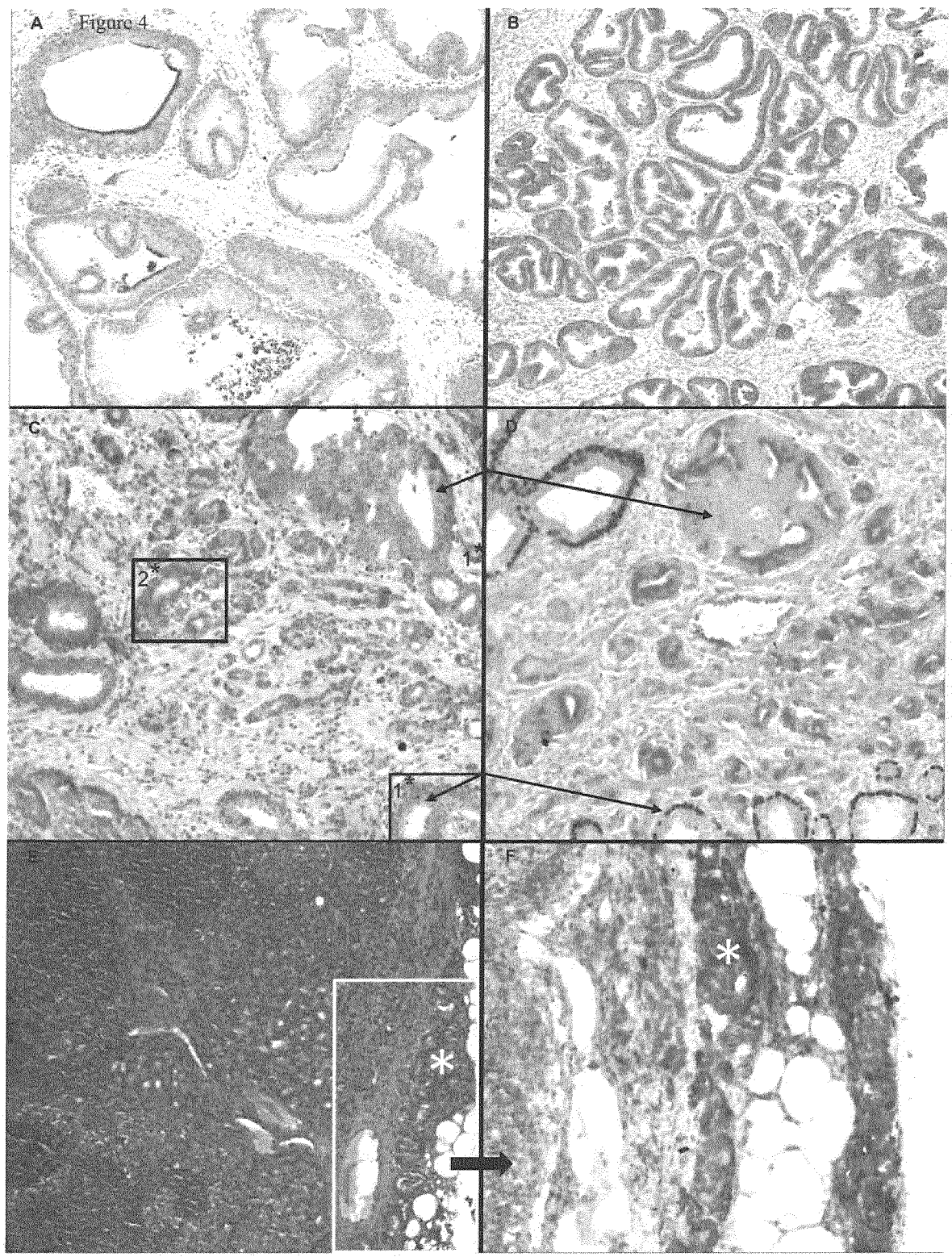
FIG. 4. Expression of pmCiC in benign normal and malignant human prostatic tissues. A, B, C and F were stained with pmCiC-specific antibody. (A) Normal prostatic tissue with prominent staining of epithelial cells surrounding the lumen, in particular their apical side. (B) Benign prostatic hyperplasia with significant staining of luminal prostate epithelial cells (note stronger staining vs normal tissue) (70× magnification used for both A and B). Tissue sections taken from the same cancerous gland stained for pmCiC (C) or (D) combined p63 and Racemase/P504S. Brown staining (in D) indicates p63 positive nuclear and negative Racemase/P504S cytoplasm staining characteristic for normal cells, whilst cytoplasm positive Racemase/P504S (pink) and nuclear negative p63 indicates cancer cells. Black arrows show respective areas of tissue to facilitate comparison between pmCiC versus p63-Racemase/P504S staining of cancerous and normal epithelial cells. (C and D, 170× magnification). Additionally, the areas representative for benign (1*) and cancer cells (2*) from C are enlarged and shown in Supp.
Figure 5:
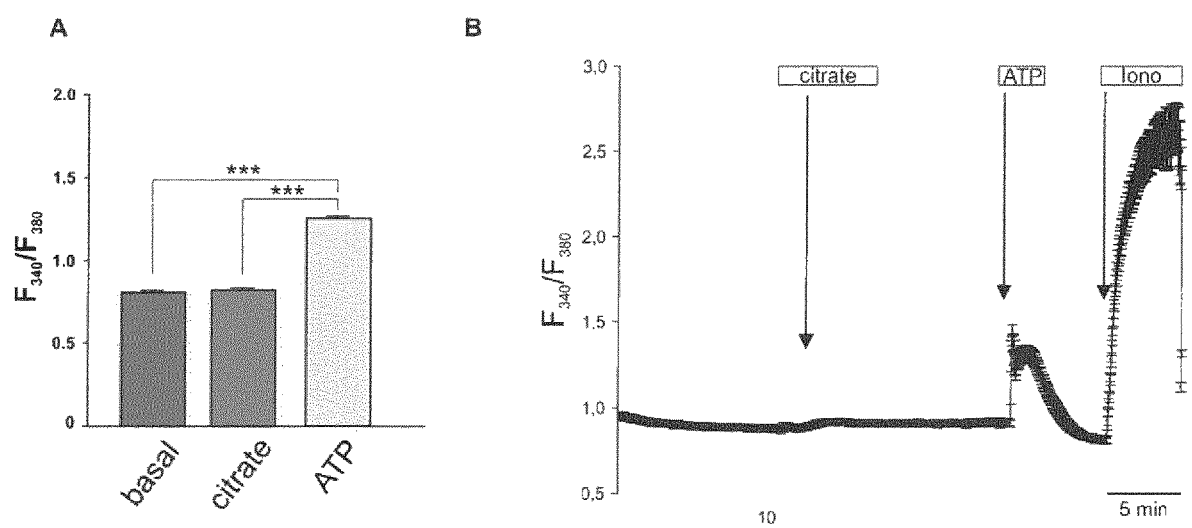
FIG. 5. (E and F) Lymph node metastasis of prostatic cells: (E, 10× magnification) lymph node with prostate cancer metastasis stained with haematoxylin and eosin and (F) the same tissue stained with pmCiC. The sequentially sectioned area of the same tissue is indicated with the white frame. Metastatic prostate cancer cells show expression of pmCiC in (F, 150× magnification). White stars on both photos indicate the same area of the lymph node.
Figure 6:
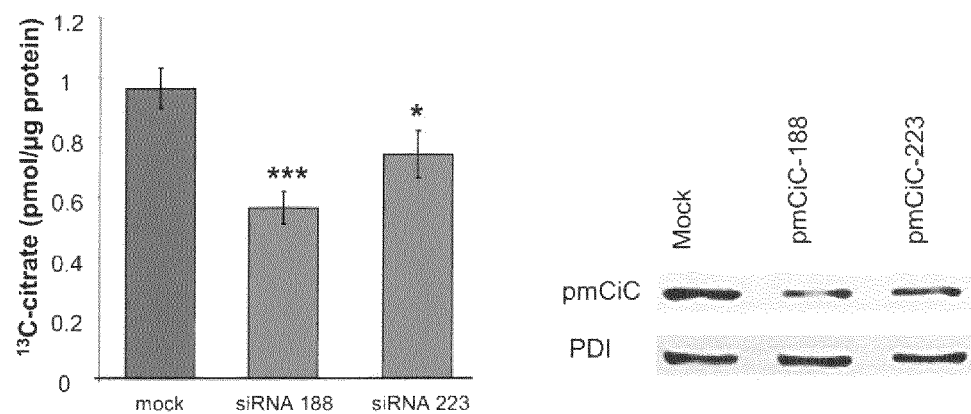
FIG. 6. (left) Intracellular $^{13}$C-citrate content of PC-3M cells transiently transfected with two different siRNAs against pmCiC. 48 h after transfection, the cells were incubated with 200 mM $^{13}$C-citrate for 24 h. (right) Western blot analysis of pmCiC protein in PC-3M cells 48 h after transfection; pmCiC-188 and 223 refer to the siRNA-targeted base. (*P<0.05, ***P<0.005; n=5).
Figure 9:
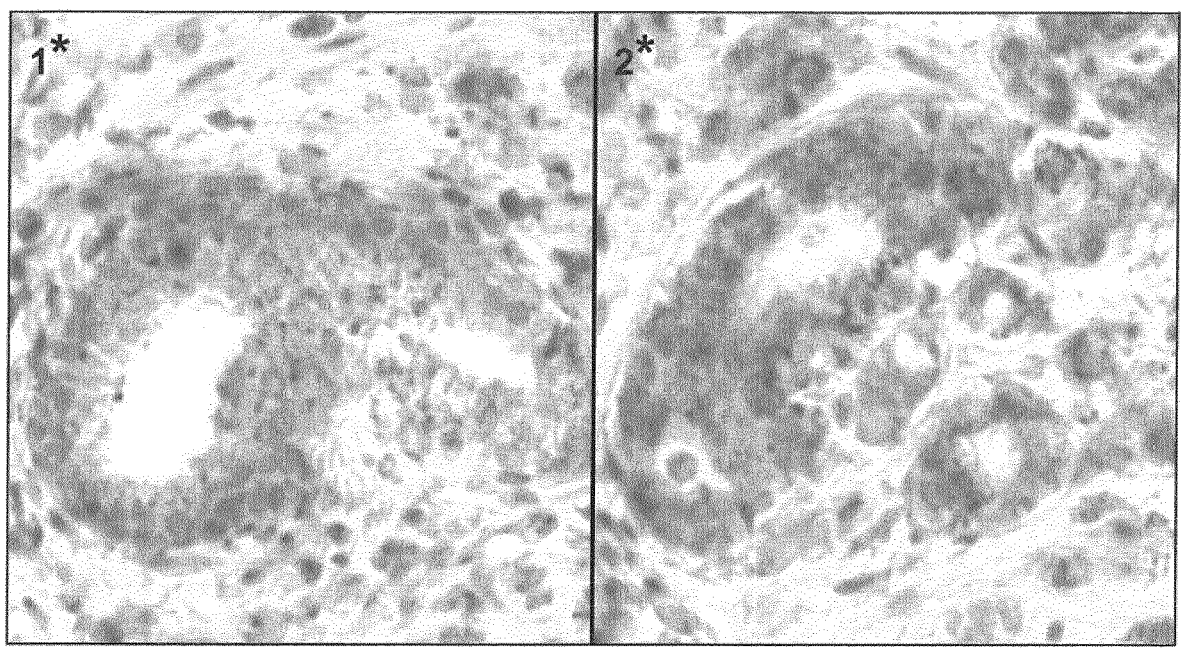
FIG. 9. Enlarged areas from FIG. 4C (640× magnification) showing differences in the intensity and pattern of staining of pmCiC between benign epithelial (1*) and cancerous cells (2*).
Figure 10:
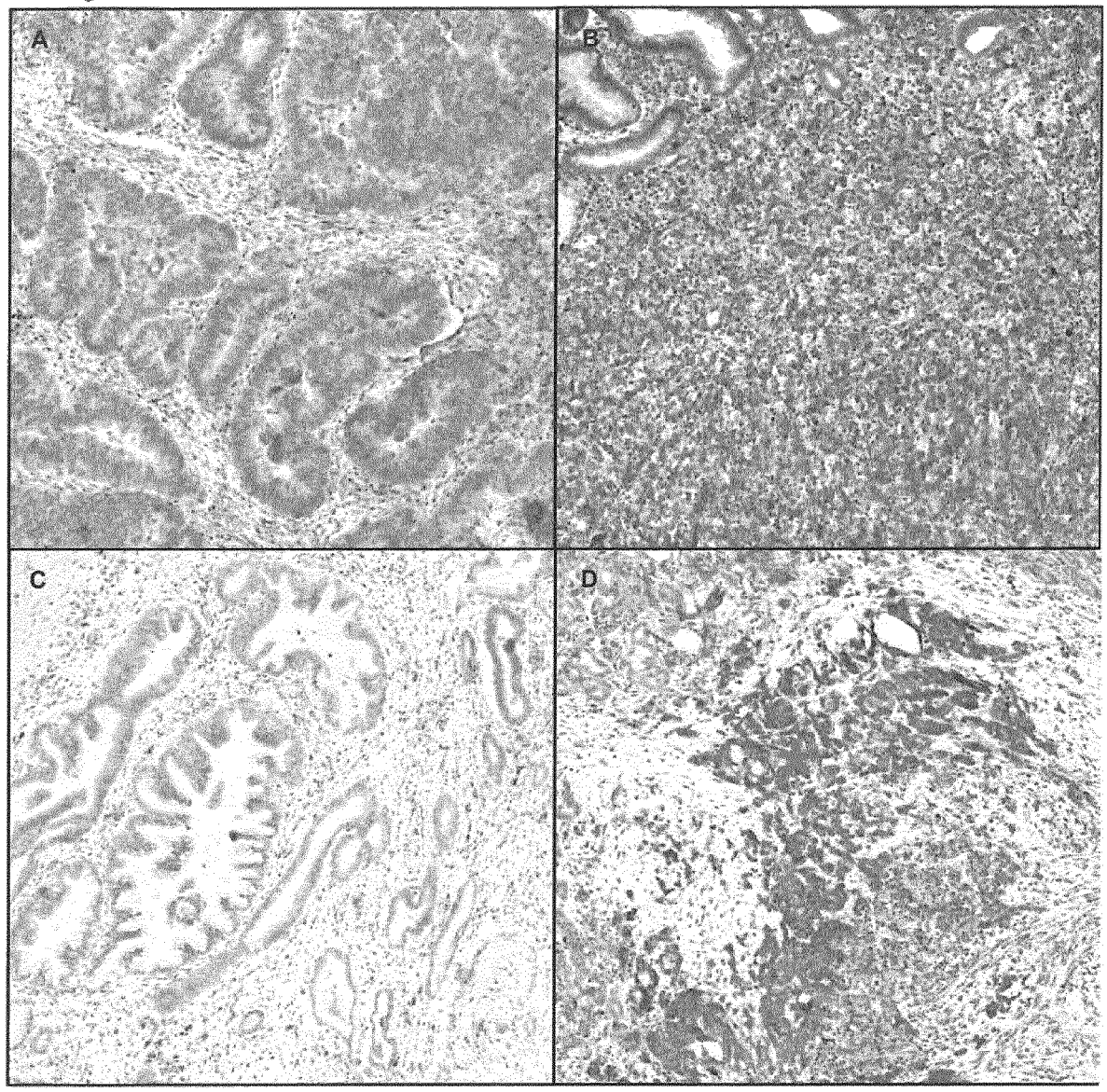
FIG. 10. pmCiC expression in cancerous tissues of different origin. (A,B-gastric cancer). Gastric adenocarcinoma, intestinal (glandular) type with irregular tubular structures is shown in (A). pmCiC staining in this subtype is weak, focal and patchy (predominantly apical), as compared to the gastric adenocarcinoma, diffuse type (B) with almost all signet-ring cells strongly stained with pmCiC. (C,D-pancreatic cancer). (C) moderately differentiated pancreatic ductal adenocarcinoma cells stain heterogeneous and weakly positive in the cytoplasm (D), whereas poorly differentiated pancreatic ductal adenocarcinomas (*) are strongly positive in a diffuse pattern (A-D: 100-× magnification).

To confirm the relevance of the present findings to human carcinogenesis, expression of pmCiC in various human tissues was evaluated by immunohistochemistry (INC). Benign normal prostatic epithelium showed pmCiC staining predominantly in the apical part of the cells (FIG. 4A). pmCiC staining intensity in epithelial cells is increased in BPH (benign prostatic hyperplasia), correlating with elevated extracellular citrate levels associated with benign prostatic overgrowth[19] (FIG. 4B). Importantly, diffuse and strong staining of pmCiC is also observed in cancer cells (FIG. 4C) and correlated well with p63/Racemase/P504S cocktail staining[20] (double-staining method, FIG. 4D). Benign prostatic epithelium with characteristic nuclear p63 positivity[20] (shown in FIG. 4D) stained weakly with pmCiC (FIG. 4C and FIG. 9). In contrast, prostatic adenocarcinoma staining with pmCiC is stronger and more evenly dispersed (FIG. 4C and FIG. 9), correlating with cytoplasmic Racemase/P504S positivity (FIG. 4D). Cancer cells also retain high expression levels of pmCiC at lymph node metastasis sites (FIGS. 4E and F). Immunohistochemical staining of pmCiC is also positive in other cancerous tissues, including pancreatic and gastric adenocarcinomas (FIG. 10). Obtained in this study data suggest correlation between the intensity of pmCiC staining and tumour subtype (FIG. 4 and FIG. 9, 10) and the correlation of pmCiC expression with cancer aggressiveness.

Figure 11:
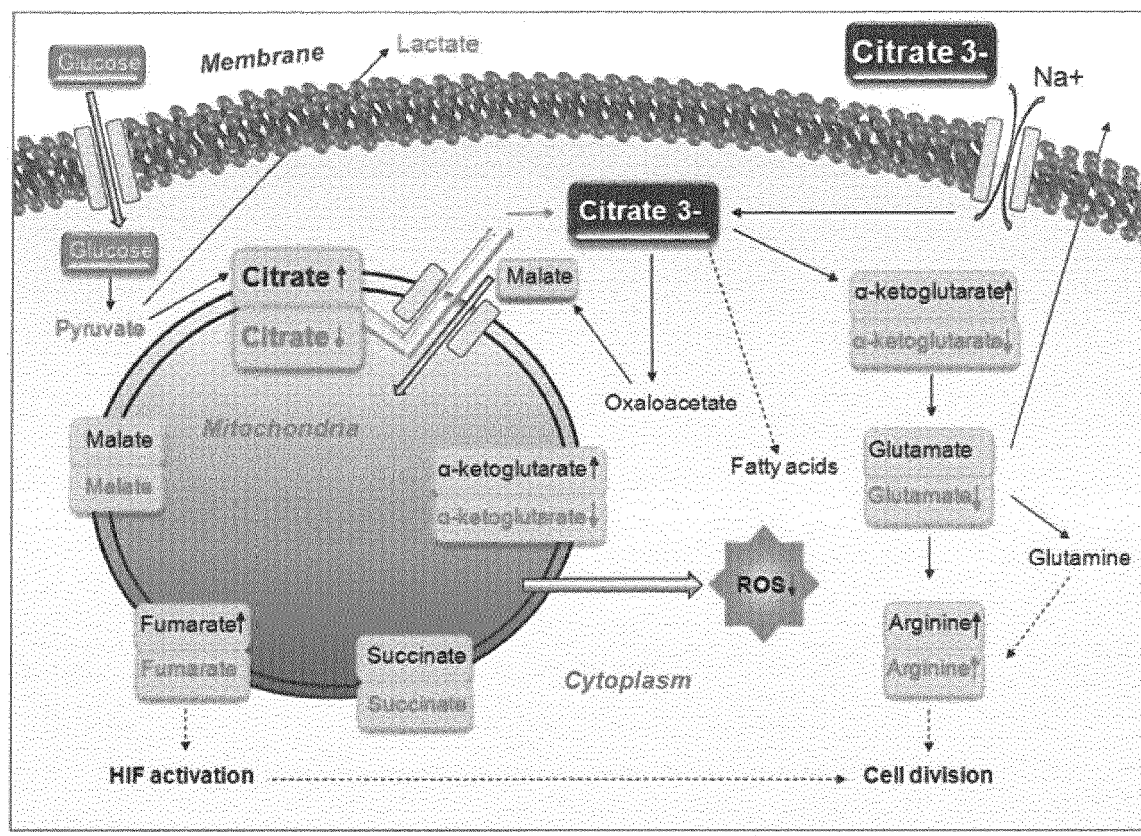
FIG. 11. Scheme of metabolic pathways that interact with extracellular citrate based on the present research and previously published data. Red colour depicts labelled substrates derived from $^{13}$C glucose; black represents unlabelled intermediates derived from unlabelled citrate. Decrease or increase in the substrate abundance shown with arrows illustrate the changes determined in cells incubated with 200 mM extracellular citrate compared to control conditions (without extracellular citrate). Unlabelled citrate (black) is taken up by cancer cells through pmCiC and enters primarily cytosolic pathways. We hypothesise that this in-turn reduces mitochondrial citrate production and decreases ROS synthesis. More efficient Krebs cycle activity (with decreased need for citrate supply to cytoplasm) allows for fumarate accumulation potentially resulting in HIF activation and cell division[15]. Sufficient citrate supply stimulates arginine synthesis, facilitating processes such as cell division. Because of reduced mitochondrial activity more pyruvate is metabolised into lactate and less glucose consumed.
Figure 12:
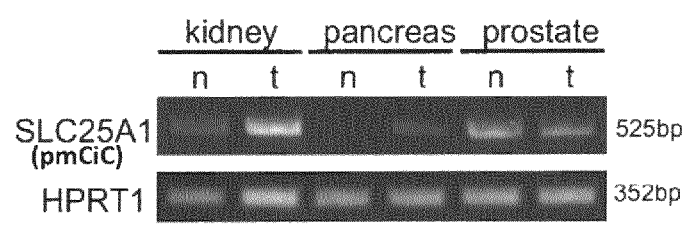
FIG. 12. pmCiC mRNA expression in human tissues free of cancer (n) and with cancer (t). The mRNA expression is significantly increased.

Our study shows that extracellular citrate at physiological concentrations affects overall cancer cell metabolism (as summarised in FIG. 11). We have focused primarily on tumours originating from prostate because healthy prostatic cells are known to release a large amount of citrate, whilst citrate disappears from the gland when prostate growth becomes metastatic[21]. Changes in prostate cell metabolism (e.g. decreased expression of $Zn^{2+}$ transporters and increased activity of mitochondrial aconitase) have been suggested to account for extracellular citrate fluctuations[22]. However, our data offer an additional explanation for the decrease in extracellular citrate–citrate is taken up by malignant cells. This metabolic utilization of extracellular citrate: (1) reduces Krebs cycle activity, (2) allows for fumarate accumulation, (3) reduces glucose consumption, (4) increases crucial amino acid levels including arginine or proline, and (5) decreases ROS synthesis.

Importantly, all of these observed changes have been previously shown to correlate with aggressiveness of cancer cells[23,24], allowing for support of processes such as metabolism under stress (hypoxia) and cell proliferation; accordingly expression of the pmCiC correlates with the severity of cancer grade in the human cancers the inventors studied. We conclude that this plasma membrane transporter should be recognised in the search for potential novel targets in cancer therapy.

Experimental Procedures
Cell Culture, PCR and Western Blotting

Cell lines were grown as described previously[13,14,25]. The following chemicals were used: uniformly $^{13}C$-labelled citric acid and glutamine and unlabelled citric acid (Sigma, St. Louis, Mo., USA), uniformly $^{13}C$-labelled glucose (Cambridge Isotope Laboratories, Andover, Mass., USA), dialysed serum (PAN Biotech GmbH, Aidenbach, Germany) anti mCiC and pmCiC antibody[14] (mitochondrial citrate carrier, GenScript Inc., Piscataway, N.J., USA). Western blotting[25] and PCR[14] were performed as described before. Experimental media consisted of RPMI-1640, 5% dialysed serum, 2 mM glutamine, 25 mM glucose±200 µM, citrate unless otherwise stated. The incubation time varied between 24-72 h as specified. For the extraction of the plasma membrane protein the Plasma Membrane Protein Extraction Kit (Abcam, Cambridge, UK) was used. The purity of the extraction was verified by checking for the presence of mCiC and Tom40 in the extract.

Uptake Experiments and Metabolomics

Metabolites were extracted with 80% methanol and measured by HPLC-ESI-MS/MS on an AB SCIEX (Framingham, Mass., USA) Q TRAP™ 4000 system. Multiple reaction monitoring (MRM) with one transition each for the unlabelled analyte and the labelled analogue(s) was used. Amino acids were derivatized using propyl chloroformate/propanol as recently described[26]. Krebs cycle intermediates were separated on a Phenomenex Luna NH2 (150×2 mm i.d., 3 µm, Torrence, Calif., USA) column with a water (0.1% (v/v) formic acid)/acetonitrile gradient and ionized in negative mode. Lactate and glucose in the media were measured as previously described[27].

Transient siRNA Transfections and Radiolabelled Citrate Uptake $^{14}C$ citrate was purchased from Moravek Biochemicals (Brea, Canada) and experiments were performed as described[14]. For transient siRNA transfections, cells were preincubated with chloroquine for 2 h. This was followed by 24 h incubation with either siRNA or mock solution. Western blot analysis or uptake measurements were performed as described in other sections of Materials and Methods.

Immunohistochemistry

Human tissue was stained with the pmCiC antibody as described before[14].

Flow Cytometry (ROS and Cell Cycle Measurement)

Studies were performed as before[28]. For cell cycle analysis incubation with RNase A was followed by propidium iodine staining (Sigma Aldrich, Germany). ROS production was detected with dihydrorhodamine 123 (Molecular Probes, Darmstadt, Germany). Analysis was performed using a FACSCanto (Becton Dickinson, Franklin Lakes, N.J., USA) flow cytometer. At least 10,000 live cells were measured per sample. Dead cells were detected using the Aqua Live/Dead cell kit (Molecular Probes).

Proliferation

Cell numbers were assessed using a hemocytometer and trypan blue exclusion dye. Microscopic cell counts were performed by 3 independent investigators.

Calcium Imaging

The experiments were performed using a ZEISS live cell imaging setup (ZEISS, Jena, Germany). Fura-2/AM-loaded cells (2 µM, 45 min at 37° C.) were illuminated with light of 340 or 380 nm (BP 340/30 HE, BP 387/15 HE) using a fast wavelength switching and excitation device (Lambda DG-4, Sutter Instrument, Novato, Calif., USA). Fluorescence was detected at 510 nm (BP 510/90 HE and FT 409) using an AxioCam MRm CCD camera (ZEISS). ZEN 2012 software (ZEISS) was used to control the hardware and acquire data.

Calculations and Statistics

Percentage differences denote change of the experimental values as compared to the control data (considered to be 100%). Data are presented as mean±SD, number of replicates n≥5. Statistical significance was assessed using a two-tailed t-test.

Gluconate-Inhibitor of pmCiC

Several lines of evidence presented below indicate gluconate as an inhibitor of pmCiC.

Figure 13:
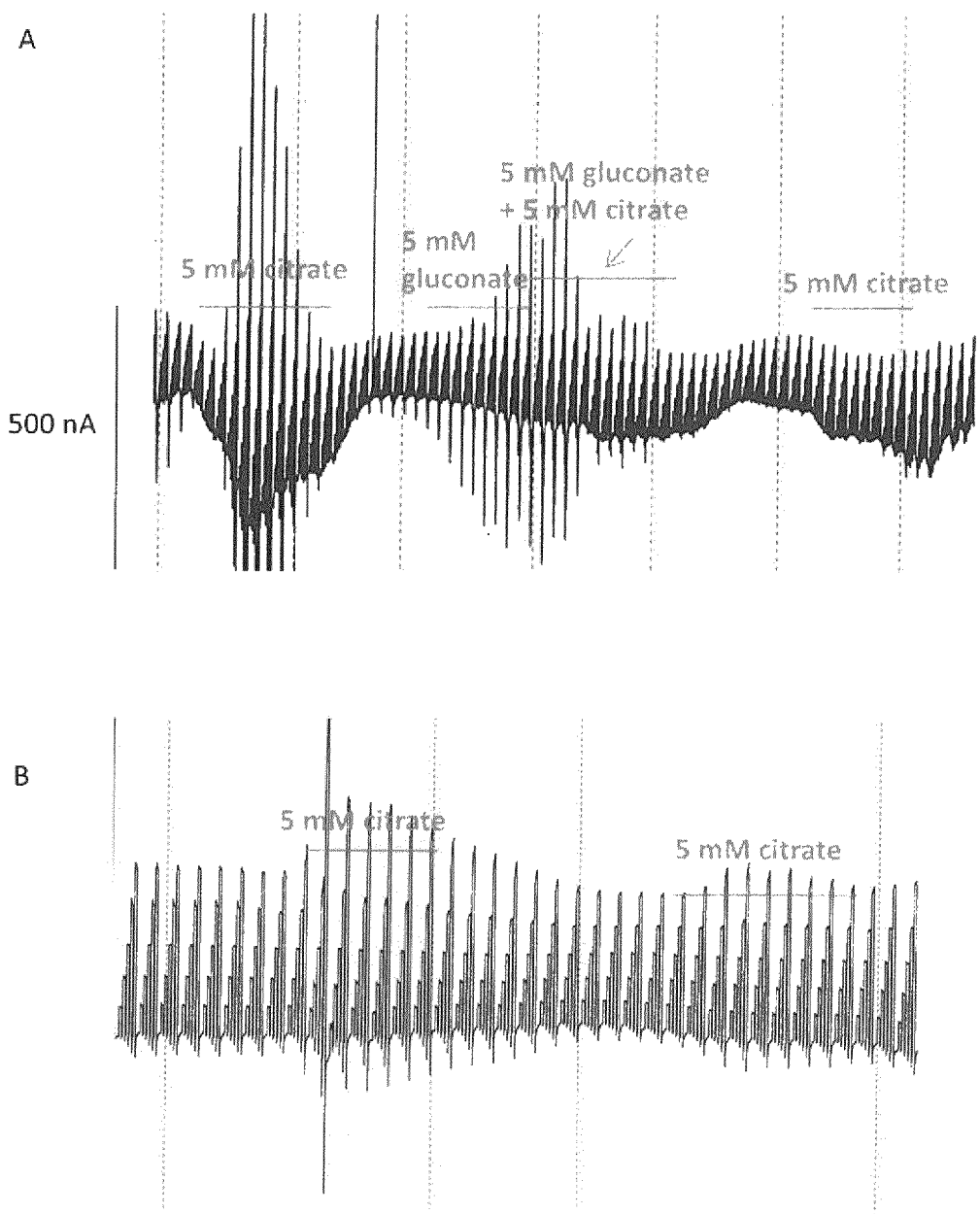
FIG. 13. Oocytes were injected with either pmCiC cDNA (A) or water (B). Citrate induced current was observed only in the oocytes with pmCiC expressed, whilst water-injected oocytes did not show any citrate induced current. Application of gluconate reduced significantly citrate induced current (A); this effect was irreversible as application of citrate after gluconate treatment induced a much smaller current as compared to citrate-induced current observed in oocytes before gluconate application.

1. pmCiC expression in oocytes—two electrodes voltage clamp (FIG. 13)

We have expressed pmCiC in oocytes and induced citrate inward current by introducing citrate into extracellular media. When applied extracellularly in the presence of gluconate, citrate-induced current is significantly decreased. This reduction was irreversible, as subsequent application of citrate after gluconate removal from the media was not able to restore the primary response.

Figure 14:
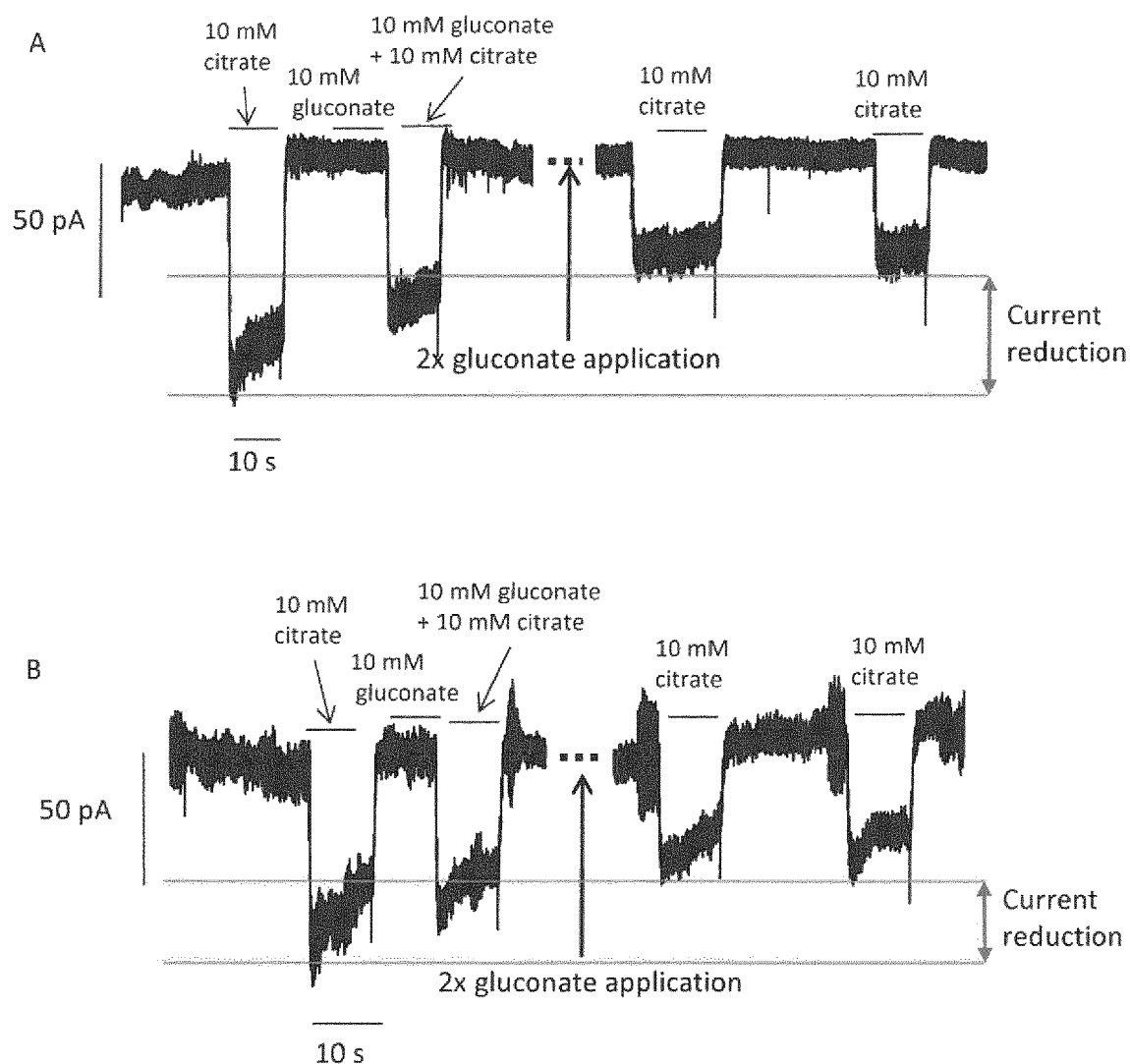
FIG. 14. Patch clamp recordings were performed on PC-3M (A) and PNT2-C2 (B) cells. Citrate-induced current was observed in both cell lines, however, the current was greater in the case of cancer cells (A). Application of 10 mM gluconate followed by application of 10 mM citrate in the presence of 10 mM gluconate resulted in reduced citrate-induced current. Importantly, reduction in citrate-induced current in the presence of gluconate was irreversible. Moreover, repeated application of gluconate resulted in increased reduction of citrate-induced current. The effect of reduced citrate-induced current was greater in the case of PC-3M cells versus PNT2-C2 cells.

2. Patch clamp on human prostate cancer PC-3M and benign PNT2-C2 cells (FIG. 14)

Extracellular application of citrate induced inward current in both cell lines as described earlier. Here we show that similar to the case of oocytes when applied in the presence of gluconate, citrate-induced current is decreased. Importantly, repeated application of gluconate results in further citrate-induced current reduction. As in the case of oocytes, gluconate inhibition of citrate-induced current was irreversible. Repeated application of citrate on PC-3M cells has been previously shown not to cause any reduction in citrate current (Mycielska et al., 2005).

Figure 15:
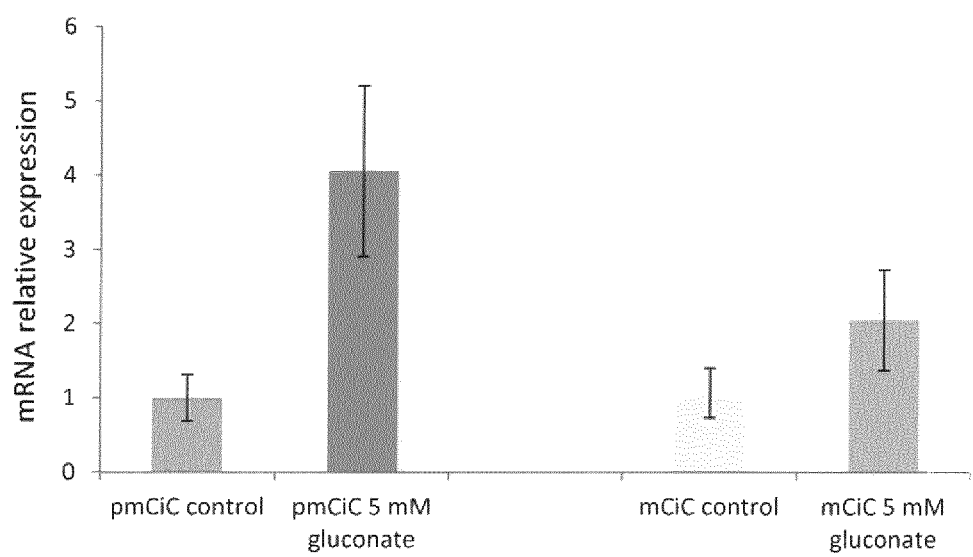
FIG. 15. Metastatic human prostate cancer PC-3M cells were grown with extracellular citrate in the presence or absence of gluconate (5 mM). RealTime PCR was performed to assess changes to the mRNA expression level of pmCiC and mCiC.
Figure 16:
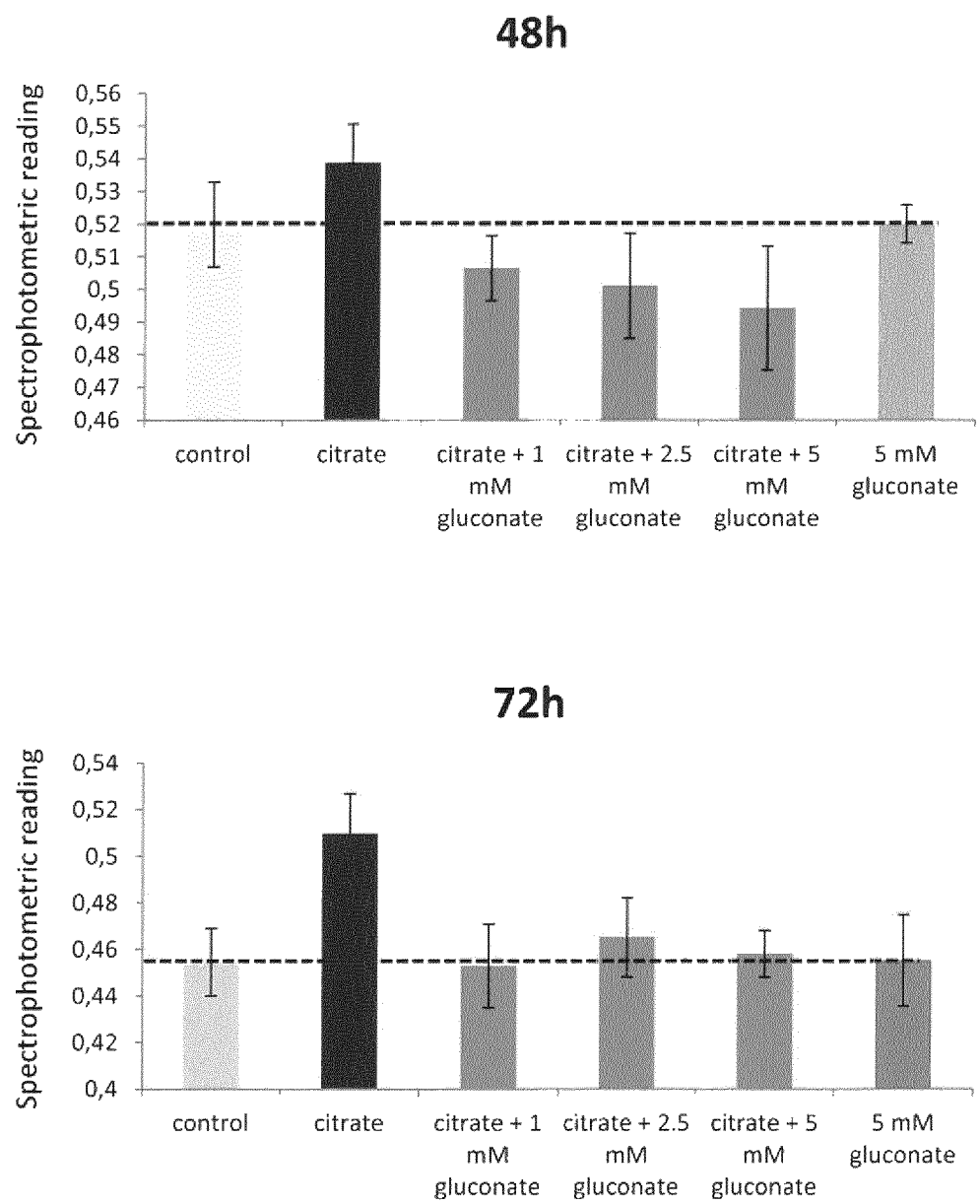
FIG. 16. Metastatic human prostate cancer PC-3M cells were grown in RPMI media supplemented with 0.5 g/L glucose and glutamine. Their survival rate was measured after 48 h and 72 h using an MTT assay. The control depicts survival of the cells with no extracellular citrate or glutamate.
Figure 17:
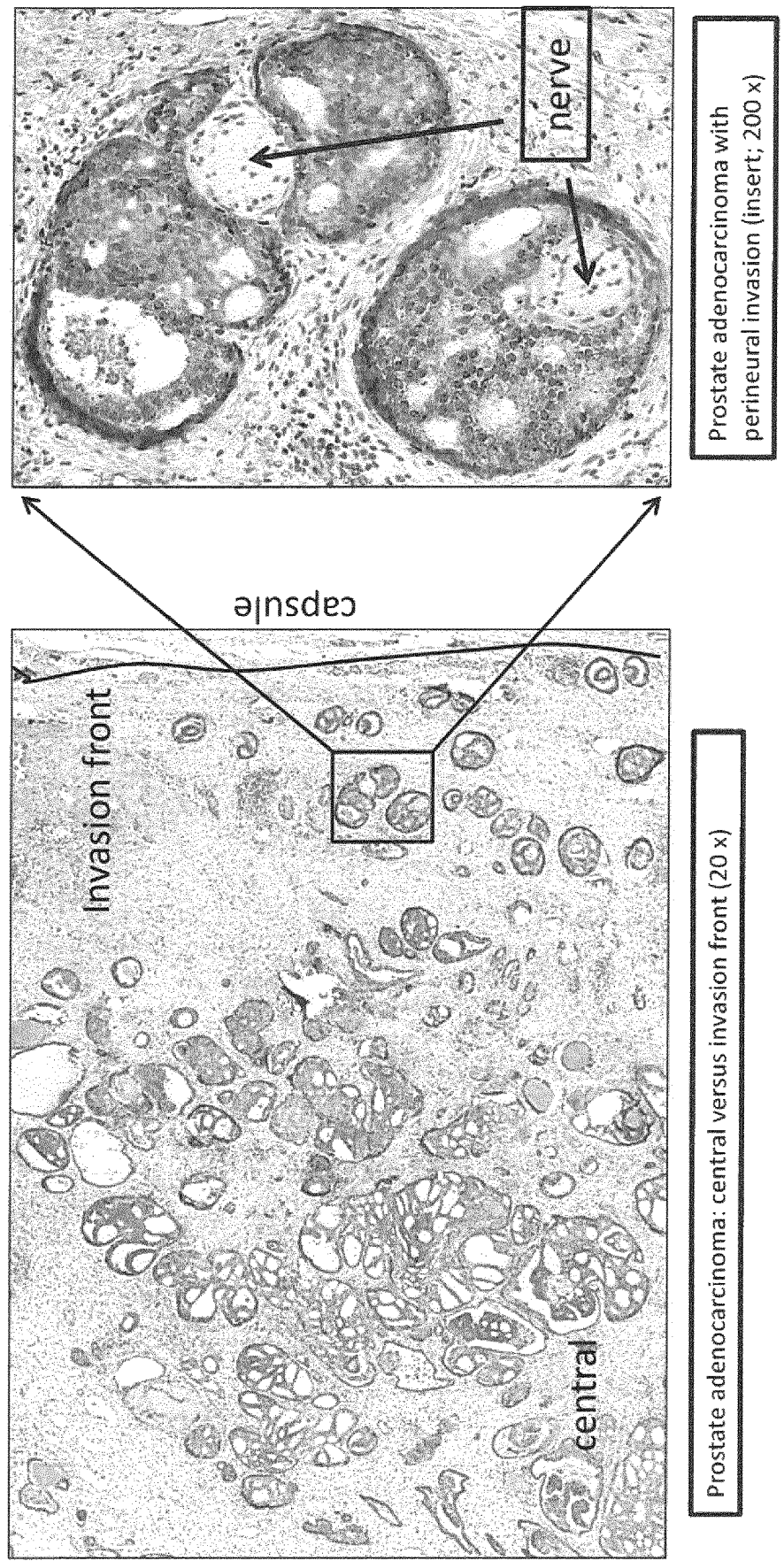
FIG. 17. pmCiC expression in prostatic tissue. Prostate adenocarcinoma, with differentially stained cancer cells. The cells show stronger staining at the invasion front as compared to the central part. On the right enlarged insert showing perineural invasion. Again the cells show stronger staining.

3. Effects of extracellular gluconate on pmCiC mRNA expression (FIG. 15)

We have studied the effect of gluconate in the extracellular media supplemented with citrate on the expression changes of pmCiC and mCiC as compared to the control conditions where the cells were incubated with extracellular citrate only. The Human metastatic prostate PC-3M cells incubated in media supplemented with 5 mM gluconate have shown significantly increased pmCIC and mCiC mRNA expression (FIG. 15). This result would suggest a cellular adaptation to compensate for the loss of citrate intake due to gluconate inhibition. On the other hand, there was a significant mCiC mRNA increase, which would indicate increased mitochondrial activity to maintain intracellular citrate level.

4. Effect of gluconate on the survival of human prostate cancer PC-3M cells (16)

Results show that 200 µM of extracellular citrate increases survival of cancer cells incubated under stress conditions (in serum-free media with 0.5 g/L gluc). Importantly, in the presence of gluconate, this protective effect of extracellular citrate is abolished and the survival of cells is the same as in the absence of extracellular citrate. Importantly, gluconate has no effect on cell survival in the absence of extracellular citrate.

LITERATURE

1. Vander Heiden, M. G., Cantley, L. C. & Thompson, C. B. Understanding the Warburg effect: the metabolic requirements of cell proliferation. *Science* 324, 1029-1033 (2009).

2. Currie, E., Schulze, A., Zechner, R., Walther, T. C. & Farese, R. V. Jr. Cellular Fatty Acid metabolism and cancer. *Cell. Metab.* 18, 153-161 (2013).

3. Liu, Y. Fatty acid oxidation is a dominant bioenergetic pathway in prostate cancer. *Prostate Cancer Prostatic Dis.* 9, 230-234 (2006).

4. Holla, V. R, Wu, H., Shi, Q., Menter, D. G & DuBois, R. N. Nuclear orphan receptor NR4A2 modulates fatty acid oxidation pathways in colorectal cancer. *J. Biol. Chem.* 286, 30003-30009 (2011).

5. Linher-Melville, K. et al. Establishing a relationship between prolactin and altered fatty acid β-oxidation via carnitine palmitoyl transferase 1 in breast cancer cells. *BMC Cancer* 4, 11-56 (2011).

6. Migita, T. et al. ATP citrate lyase: activation and therapeutic implications in non-small cell lung cancer. *Cancer Res.* 68, 8547-8554 (2008).

7. Frezza, C. & Gottlieb, E. Mitochondria in cancer: not just innocent bystanders. Semin. *Cancer Biol.* 19, 4-11 (2009).

8. Metallo, C. M. et al. Reductive glutamine metabolism by IDH1 mediates lipogenesis under hypoxia. *Nature* 481, 380-384 (2011).

9. Rocha, C. M. et al. Metabolic signatures of lung cancer in biofluids: NMR-based metabonomics of blood plasma. *J. Proteome Res.* 10, 4314-4324 (2011).

10. Cao, M., Zhao, L., Chen, H., Xue, W. & Lin, D. NMR-based metabolomic analysis of human bladder cancer. *Anal. Sci.* 28, 451-456 (2012).

11. Zhang, L. et al. Distinguishing pancreatic cancer from chronic pancreatitis and healthy individuals by (1)H nuclear magnetic resonance-based metabonomic profiles. *Clin. Biochem.* 45, 1064-1069 (2012).

12. Clyne, M. Prostate cancer: Biopsy citrate concentration could predict prostate cancer growth rate. *Nat. Rev. Urol.* 9, 123. (2012).

13. Mycielska, M. E., Palmer, C. P., Brackenbury, W. J. & Djamgoz, M. B. Expression of Na+-dependent citrate transport in a strongly metastatic human prostate cancer PC-3M cell line: regulation by voltage-gated Na+ channel activity. *J. Physiol.* 563, 393-408 (2005).

14. Mazurek, M. P. et al. Molecular origin of plasma membrane citrate transporter in human prostate epithelial cells. *EMBO Rep.* 11, 431-437 (2010).

15. Ratcliffe, P. J. Fumarate hydratase deficiency and cancer: activation of hypoxia signaling? *Cancer Cell.* 11, 303-305. (2007).

16. Marin-Valencia, I. et al. Analysis of tumor metabolism reveals mitochondrial glucose oxidation in genetically diverse human glioblastomas in the mouse brain in vivo. *Cell Metab.* 15, 827-837 (2012).

17. Son, J. et al. Glutamine supports pancreatic cancer growth through a KRAS-regulated metabolic pathway. *Nature* 496, 101-105 (2013).

18. Jang, S. W. et al. Serine/arginine protein-specific kinase 2 promotes leukemia cell proliferation by phosphorylating acinus and regulating cyclin A1. *Cancer Res.* 68, 4559-4570 (2008).

19. Costello, L. C. & Franklin, R. B. Citrate metabolism of normal and malignant prostate epithelial cells. *Urology* 50, 3-12 (1997).

20. Evans, A. J. Alpha-methylacyl CoA racemase (P504S): overview and potential uses in diagnostic pathology as applied to prostate needle biopsies. *J. Clin. Pathol.* 56, 892-897 (2003).

21. Serkova, N. J. et al. The metabolites_citrate, myo-inositol, and spermine are potential age-independent markers of prostate cancer in human expressed prostatic secretions. *Prostate* 68, 620-628 (2008).

22. Singh, K. K., Desouki, M. M., Franklin, R. B. & Costello, L. C. Mitochondrial aconitase and citrate metabolism in malignant and nonmalignant human prostate tissues. *Mol. Cancer* 4, 5-14 (2006).

23. Cardaci, S. & Ciriolo, M. R. TCA Cycle Defects and Cancer: When Metabolism Tunes Redox State. *Int. J. Cell Biol.* 2012, 161837 (2012).

24. Cuperlovic-Culf, M., Culf, A. S., Touaibia, M. & Lefort, N. Targeting the latest hallmark of cancer: another attempt at 'magic bullet' drugs targeting cancers' metabolic phenotype. *Future Oncol.* 8, 1315-1330 (2012).

25. Lang, S. A. et al. Mammalian target of rapamycin is activated in human gastric cancer and serves as a target for therapy in an experimental model. *Int. J. Cancer.* 120, 1803-1810 (2007).

26. Van der Goot, A. T. et al. Delaying aging and the aging-associated decline in protein homeostasis by inhibition of tryptophan degradation. *PNAS* 109, 14912-14917 (2012).

27. Dettmer, K. et al. Distinct metabolic differences between various human cancer and primary cells. *Electrophoresis* 34, 2836-2847 (2013).

28. Lantow, M., Viergutz, T., Weiss, D. G. & Simko. M. Comparative study of cell cycle kinetics and induction of apoptosis or necrosis after exposure of human Mono Mac 6 cells to radiofrequency radiation. *Radiat. Res.* 166, 539-543 (2006).

The invention claimed is:

1. A method of treating cancer in a patient in need thereof, the method comprising administering to the patient an inhibitor of plasma membrane citrate transporter (pmCiC) activity, wherein said cancer is selected from the group consisting of prostate cancer, gastric cancer, pancreatic cancer, breast cancer, and colon cancer and wherein said inhibitor of pmCiC activity is gluconate.

2. The method of claim 1, wherein the treatment comprises administering gluconate to a cancer patient in a physiologically suitable dosage form, thereby promoting cancer cell death.

* * * * *

SEQUENCE LISTING

```
<160> NUMBER OF SEQ ID NOS: 1

<210> SEQ ID NO 1
<211> LENGTH: 318
<212> TYPE: PRT
<213> ORGANISM: Homo sapiens

<400> SEQUENCE: 1

Met Phe Pro Ala Ala Leu Ala Arg Arg Pro Arg Arg Pro Lys Ser Gly
1               5                   10                  15

Thr Gly Glu Gly Pro Glu Arg Gln Arg Pro Gly Gly Ser Leu Arg Ser
            20                  25                  30

Gly Phe Pro Val Pro Ala Gly Gly Leu Ala Gly Gly Ile Glu Ile Cys
        35                  40                  45

Ile Thr Phe Pro Thr Glu Tyr Val Lys Thr Gln Leu Gln Leu Asp Glu
    50                  55                  60

Arg Ser His Pro Pro Arg Tyr Arg Gly Ile Gly Asp Cys Val Arg Gln
65                  70                  75                  80

Thr Val Arg Ser His Gly Val Leu Gly Leu Tyr Arg Gly Leu Ser Ser
                85                  90                  95

Leu Leu Tyr Gly Ser Ile Pro Lys Ala Ala Val Arg Phe Gly Met Phe
            100                 105                 110

Glu Phe Leu Ser Asn His Met Arg Asp Ala Gln Gly Arg Leu Asp Ser
        115                 120                 125

Thr Arg Gly Leu Leu Cys Gly Leu Gly Ala Gly Val Ala Glu Ala Val
    130                 135                 140

Val Val Val Cys Pro Met Glu Thr Ile Lys Val Lys Phe Ile His Asp
145                 150                 155                 160

Gln Thr Ser Pro Asn Pro Lys Tyr Arg Gly Phe Phe His Gly Val Arg
                165                 170                 175

Glu Ile Val Arg Glu Gln Gly Leu Lys Gly Thr Tyr Gln Gly Leu Thr
            180                 185                 190
```

```
Ala Thr Val Leu Lys Gln Gly Ser Asn Gln Ala Ile Arg Phe Phe Val
    195                 200                 205

Met Thr Ser Leu Arg Asn Trp Tyr Arg Gly Asp Asn Pro Asn Lys Pro
    210                 215                 220

Met Asn Pro Leu Ile Thr Gly Val Phe Gly Ala Ile Ala Gly Ala Ala
225                 230                 235                 240

Ser Val Phe Gly Asn Thr Pro Leu Asp Val Ile Lys Thr Arg Met Gln
                245                 250                 255

Gly Leu Glu Ala His Lys Tyr Arg Asn Thr Trp Asp Cys Gly Leu Gln
            260                 265                 270

Ile Leu Lys Lys Glu Gly Leu Lys Ala Phe Tyr Lys Gly Thr Val Pro
        275                 280                 285

Arg Leu Gly Arg Val Cys Leu Asp Val Ala Ile Val Phe Val Ile Tyr
    290                 295                 300

Asp Glu Val Val Lys Leu Leu Asn Lys Val Trp Lys Thr Asp
305                 310                 315
```